United States Patent
Hu et al.

(10) Patent No.: US 11,783,924 B2
(45) Date of Patent: *Oct. 10, 2023

(54) ECG INFORMATION PROCESSING METHOD AND ECG WORKSTATION

(71) Applicant: Shanghai Lepu CloudMed Co., Ltd, Shanghai (CN)

(72) Inventors: Chuanyan Hu, Beijing (CN); Jun Cao, Beijing (CN); Chang Liu, Beijing (CN); Zifang Zhao, Changping District Beijing (CN); Xue Zhang, Beijing (CN); Baoquan Wang, Beijing (CN)

(73) Assignee: Shanghai Lepu CloudMed Co., Ltd, Shanghai (CN)

( * ) Notice: Subject to any disclaimer, the term of this patent is extended or adjusted under 35 U.S.C. 154(b) by 480 days.

This patent is subject to a terminal disclaimer.

(21) Appl. No.: 16/766,551

(22) PCT Filed: Apr. 18, 2018

(86) PCT No.: PCT/CN2018/083466
§ 371 (c)(1),
(2) Date: May 22, 2020

(87) PCT Pub. No.: WO2019/161611
PCT Pub. Date: Aug. 29, 2019

(65) Prior Publication Data
US 2021/0280281 A1    Sep. 9, 2021

(30) Foreign Application Priority Data

Feb. 24, 2018   (CN) .......................... 201810157365.3

(51) Int. Cl.
*G16H 10/60*   (2018.01)
*G16H 40/63*   (2018.01)

(52) U.S. Cl.
CPC ............. *G16H 10/60* (2018.01); *G16H 40/63* (2018.01)

(58) Field of Classification Search
None
See application file for complete search history.

(56) References Cited

U.S. PATENT DOCUMENTS

| 6,463,320 | B1 | 10/2002 | Xue et al. | |
| 8,684,942 | B2* | 4/2014 | Zhang | A61B 5/352 |
| | | | | 600/508 |

(Continued)

FOREIGN PATENT DOCUMENTS

| CN | 1850000 A | 10/2006 |
| CN | 102028459 B | 1/2013 |

(Continued)

OTHER PUBLICATIONS

Casarella, J. M. (2013). The classification of un-preprocessed ECG waveforms through the application of the hierarchical temporal memory model (Order No. 3569129). Available from ProQuest Dissertations and Theses Professional. (1347669889). (Year: 2013).*

(Continued)

*Primary Examiner* — Jason S Tiedeman
*Assistant Examiner* — Emily Huynh
(74) *Attorney, Agent, or Firm* — TraskBritt

(57) ABSTRACT

An ECG information processing method and ECG workstation, wherein the method comprises: the ECG workstation receives the ECG data output by an ECG device, the ECG data includes ID of the measured object and the detection time information; perform ECG data analysis on the ECG data to generate report data; receive a report data query input by the user, query corresponding report data according to the user ID of the user, and generate report data query result list data; acquire the selected report data according to the (Continued)

selection instruction, determine output mode information and output format information according to the report output, and, selectively output report conclusion data, report entry data, and/or the partial data or all the data in the report graphic data, and convert the partial data or all the data in data format according to the output format information, to generate report output data.

9 Claims, 14 Drawing Sheets

(56) References Cited

U.S. PATENT DOCUMENTS

| | | | |
|---|---|---|---|
| 2001/0032099 | A1 | 10/2001 | Joao |
| 2004/0230105 | A1* | 11/2004 | Geva ............... A61B 5/7275 600/509 |
| 2011/0021902 | A1* | 1/2011 | Kim .................. A61B 5/333 600/523 |
| 2014/0249437 | A1* | 9/2014 | Zong ................. A61B 5/316 600/509 |
| 2016/0045117 | A1* | 2/2016 | Liu .................. A61B 5/02405 600/502 |
| 2017/0143266 | A1 | 5/2017 | Kovacs et al. |

FOREIGN PATENT DOCUMENTS

| | | | |
|---|---|---|---|
| CN | 204813800 | U | 12/2015 |
| CN | 105320974 | A | 2/2016 |
| CN | 105380620 | A | 3/2016 |
| CN | 106529182 | A | 3/2017 |
| CN | 106815570 | A | 6/2017 |
| CN | 107714023 | A | 2/2018 |
| CN | 106027566 | B | 10/2018 |
| CN | 105286909 | B | 2/2019 |
| EP | 1110502 | A2 | 6/2001 |
| WO | WO-2011115576 | A2 * | 9/2011 ............ A61B 34/10 |

OTHER PUBLICATIONS

European Extended Search Report and Opinion for European Application No. 18907191, dated Nov. 5, 2021, 13 pages.

Chinese First Office Action for Chinese Application No. 201810157365.3 dated Jun. 12, 2020, 12 pages.

Station et al., MFC-Based Auxiliary Positioning System for Myocardial Ischemia Xintun Information Management, Chenziu's Master's Degree in Givernance, Education and Information Technology Series, Issue 1, (2015) pp. 40-65.

International Search Report for International Application No. PCT/CN2018/083466 dated Jul. 31, 2018, 2 pages.

International Written Opinion for International Application No. PCT/CN2018/083466 dated Jul. 31, 2018, 3 pages.

* cited by examiner

Electrocardiogram Analysis Report

Name: Xiong Meixiu   Gender:   Age: 0   Report ID:   Report issue time: 2017-12-21

Monitoring time: From 2016-05-05 08:22:22 To 2016-05-06 08:21:10 (Calibration voltage: 10mm/mv Paper speed: 25mm/s)
Total: 23 hours 58 minutes 48 seconds   Total interference difference 01 hours 22 minutes 54 seconds   Effective duration 22 hours 35 minutes 54 seconds

Monitoring Analysis Overview

Heart rate

| | | | |
|---|---|---|---|
| Average heart rate (bpm) 64 | | Total heart rate   86303 | |
| Maximum heart rate (bpm) 89 | Occurrence time 08:29:54 | Abnormal heart beat 9808 | Accounted for the total heart beat 11.4% |
| Minimum heart rate (bpm) 50 | Occurrence time 21:34:27 | Atrial flutter-Atrial fibrillation (accounted for the total heart beat)%   0% | |

Heart rate variability

| Sinus beat standard deviation | Detection value | RR interval mean standard deviation | Detection value |
|---|---|---|---|
| SDNN (ms) | 89 | SDANN (ms) | 73 |

Long R-R interval

| | | | |
|---|---|---|---|
| Occurrence times of long RR interval (1.5-2.0s) | 12 | Occurrence times of 3s > long RR interval > 2.0s | 0 |
| Occurrence times of 5s > long RR interval > 3s | 0 | Occurrence times of long RR interval > 5s | 0 |
| longest RR interval (s) | 1.59 | Occurrence time | 2016-05-05 20:20:33 |

Supraventricular arrhythmia event

| | | |
|---|---|---|
| Total supraventricular arrhythmia   84 | Accounted for the total heart beat  0.1% | Supraventricular premature beat 74 |
| Pairs of supraventricular premature beat 3 | Bigeminy 0 | Trigeminy 0 |
| Atrial escape beat 3 | Junctional escape beat 7 | Paroxysmal superventricular tachycardia 0 |
| 1 minute maximum supraventricular arrhythmia 3 | Paroxysmal superventricular tachycardia premature beat 0 | |
| Longest supraventricular tachycardia  Duration 0s  Occurrence time | Fastet supraventricular tachycardia (bpm) 0  Occurrence time | |

Ventricular arrhythmia event

| | | | |
|---|---|---|---|
| Total ventricular arrhythmia 8217 | Accounted for the total heart beat 9.5% | Ventricular premature beat 8216 | Paroxysmal ventricular tachycardia 0 |
| Pairs of ventricular premature beat 1 | Bigeminy 16 | | Paroxysmal ventricular tachycardia premature beat 0 |
| Ventricular escape beat 1 | Trigeminy 271 | | Tip torsional ventricular tachycardia 0 |
| Atrial flutter/Atrial fibrillation 0 | 1 minute maximum ventricular arrhythmia 24 | | |
| Longet ventricular tachycardia | Duration 0s | Occurrence time   Fastet ventricular tachycardia (bpm) 0 | Occurrence time |

Conclusion:
Basic heart rate: Sinus heart rate
Heart rate:
* Heart rate variability HRV slightly decreased
Supraventricular arrhythmia:
* Occasional supraventricular premature beat
* Occasionally in pairs
* Atrial escape beat
* Junctional escape beat
Ventricular arrhythmia:
* Ventricular premature beat
* Occasionally in pairs, partially Bigeminy, partially Trigeminy
* Ventricular escape beat

Fig. 8a

Electrocardiogram Analysis Report

Hourly Statistical List of Electrocardiogram Data

| Time | HB | HR | HR_min | HR_max | Pause | V | VE | V_sin | V_blg | V_trig | S | SE | S_sin | S_blg | S_trig | JE |
|---|---|---|---|---|---|---|---|---|---|---|---|---|---|---|---|---|
| 23:00 | 3344 | 55 | 51 | 73 | 0 | 35 | 0 | 0 | 0 | 0 | 1 | 0 | 0 | 0 | 0 | 0 |
| 00:00 | 3654 | 57 | 52 | 79 | 0 | 303 | 0 | 0 | 0 | 1 | 0 | 0 | 0 | 0 | 0 | 0 |
| 01:00 | 3890 | 57 | 53 | 68 | 0 | 637 | 0 | 0 | 0 | 1 | 0 | 0 | 0 | 0 | 0 | 0 |
| 02:00 | 4077 | 65 | 57 | 78 | 0 | 693 | 0 | 0 | 2 | 2 | 0 | 0 | 0 | 0 | 0 | 0 |
| 03:00 | 3984 | 65 | 57 | 71 | 7 | 841 | 0 | 0 | 0 | 14 | 1 | 0 | 0 | 0 | 0 | 0 |
| 04:00 | 4098 | 70 | 54 | 87 | 0 | 678 | 0 | 0 | 6 | 9 | 1 | 0 | 0 | 0 | 0 | 0 |
| 05:00 | 3564 | 61 | 52 | 79 | 0 | 123 | 0 | 0 | 0 | 3 | 5 | 0 | 0 | 0 | 0 | 0 |
| 06:00 | 3874 | 59 | 53 | 72 | 0 | 394 | 0 | 0 | 0 | 13 | 5 | 0 | 0 | 0 | 0 | 0 |
| 07:00 | 303 | 61 | 60 | 65 | 14 | 25 | 1 | 0 | 0 | 0 | 0 | 0 | 0 | 0 | 0 | 7 |
| 08:00 | 44 | 0 |  |  | 0 | 0 | 0 | 0 | 0 | 0 | 0 | 0 | 0 | 0 | 0 | 0 |

Fig. 8g

ECG INFORMATION PROCESSING METHOD AND ECG WORKSTATION

CROSS-REFERENCE TO RELATED APPLICATIONS

This application is a national phase entry under 35 U.S.C. § 371 of International Patent Application PCT/CN2018/083466, filed Apr. 18, 2018, designating the United States of America and published as International Patent Publication WO 2019/161611 A1 on Aug. 29, 2019, which claims the benefit under Article 8 of the Patent Cooperation Treaty to Chinese Patent Application Serial No. 201810157365.3, filed Feb. 24, 2018.

TECHNICAL FIELD

The present disclosure relates to the technical field of data processing, and more particularly, to an electrocardiogram information processing method and an electrocardiogram workstation.

BACKGROUND

An electrocardiogram workstation sends weak electrocardiogram signals from a human body collected by an electrocardiogram collector to a computer processing system for amplification, analysis and processing, so as to achieve the purpose of diagnosing heart diseases. The electrocardiogram workstation usually includes several parts such as a computer host, a monitor, lead wires, an electrocardiogram signal collection box and a printer. The electrocardiogram workstation has a window menu, which may be used by a clinician or operator to obtain electrocardiogram output report without esoteric operation techniques or excessive manual intervention.

Electrocardiogram monitoring performed by the electrocardiogram workstation is a common clinical medical monitoring method. The monitored electrocardiogram signals are weak currents reflected by electrical activities of myocardial cells on the body surface, and are recorded by body surface electrodes and an amplification recording system.

Automatic analysis of electrocardiogram data is involved in the electrocardiogram monitoring. However, due to the complexity and variability of electrocardiogram signals per se, it is easily interfered by various signals. During the recording process, other non-cardiogenic electrical signals, such as myoelectric signal interference caused by skeletal muscle activities, are also recorded. These signals may lead to an output of incorrect heart beat signal detection results.

In addition, the electrocardiogram signals are an embodiment of a process of myocardial electrical activities, which may reflect a large amount of information about a state of the heart. When there is a problem with the state of the heart, the electrocardiogram signals will change accordingly. At present, the accuracy of automatic analysis is far from enough, resulting in that an output electrocardiogram test report does not have a significant reference, and still depends on subjective judgments from doctors.

In addition, the existing electrocardiogram workstation has single mode for outputting the electrocardiogram test report, and it cannot meet different requirements of different users or different usage needs. Therefore, how to effectively improve the automatic analysis level of the electrocardiogram, intelligently generate and output analysis data, and meet multi-directional requirements is difficulty and challenge to be solved by the present disclosure.

BRIEF SUMMARY

In order to achieve the above purpose, the present disclosure proposes an electrocardiogram information processing method and an electrocardiogram workstation. Report data is formed through complete and fast automatic analysis of electrocardiogram data output by an electrocardiogram monitoring device; the report data may be queried and it may be output according to a requested or set output mode and data format, and update and modification of the report data is supported.

A first aspect of embodiments of the present disclosure provides an electrocardiogram information processing method, including:

receiving, by an electrocardiogram workstation, electrocardiogram data output by an electrocardiogram monitoring device, wherein the electrocardiogram data includes an ID of a tested object and detection time information;

performing electrocardiogram data analysis on the electrocardiogram data, and generating report data and storing the report data; wherein the report data includes: report conclusion data, report table item data and/or report graphic data corresponding to the ID of the tested object;

receiving a report data query instruction input by a user, querying corresponding report data according to the user ID of the user, and generating and displaying report data query result list data output; wherein the report data query result list data includes at least the ID of the tested object and the detection time information of one or more pieces of the report data obtained by the querying;

receiving a selection instruction input by the user, and acquiring selected report data according to the selection instruction; and receiving a report output instruction input by the user, determining output mode information and output format information according to the report output instruction, selectively outputting part or all of data in the report conclusion data, the report table item data and/or the report graphic data according to the output mode information, and performing data format conversion on the part or all of the data according to the output format information to generate report output data.

Preferably, after the receiving a selection instruction input by the user, and acquiring selected report data according to the selection instruction, the method further includes:

receiving report conclusion modification data and/or report table item modification data input by the user; and updating the report conclusion data according to the report conclusion modification data, and updating the report table item data according to the report table item modification data.

Preferably, the electrocardiogram data is single-lead or multi-lead time sequence data; and the performing electrocardiogram data analysis on the electrocardiogram data, and generating report data includes:

converting a data format of the electrocardiogram data into a preset standard data format by resampling, and performing a first filtering processing on converted electrocardiogram data in the preset standard data format;

performing heart beat detection processing on electrocardiogram data processed by the first filtering processing to identify multiple pieces of heart beat data included in the electrocardiogram data, each of which corresponds to a heart beat cycle, including amplitude data and starting-ending time data of corresponding P wave, QRS complex and T wave;

performing interference identification on the heart beat data according to a trained Two-class interference identification model to determine whether there is interference noise in the heart beat data with a probability value for judging the interference noise;

according to lead parameters of the heart beat data and the heart beat data, combining and generating heart beat time sequence data based on results of the interference identification and time rules; and generating heart beat analysis data according to the heart beat time sequence data;

analyzing and evaluating a signal quality of the heart beat analysis data, and obtaining a signal quality evaluation index of the heart beat analysis data;

performing feature extraction and analysis of an amplitude and time characterization data on the heart beat analysis data according to a trained heart beat classification model, to obtain primary classification information of the heart beat analysis data;

inputting the heart beat analysis data of particular heart beats in results of the primary classification information into a trained ST segment and T wave change model for identification, and determining ST segment and T wave evaluation information;

performing P wave and T wave feature detection on the heart beat analysis data according to the heart beat time sequence data to determine detailed feature information of the P wave and the T wave in each heart beat;

performing secondary classification processing on the heart beat analysis data according to electrocardiogram basic rule reference data, the detailed feature information of the P wave and the T wave and the ST segment and T wave evaluation information under the primary classification information to obtain heart beat classification information; and generating electrocardiogram event data from the heart beat analysis data according to the heart beat classification information and the electrocardiogram basic rule reference data; screening the electrocardiogram event data according to the signal quality evaluation index to obtain the report conclusion data and the report table item data; and generating the report graphic data according to typical data segments in each kind of the electrocardiogram event data.

Further preferably, the performing heart beat detection processing on electrocardiogram data processed by the first filtering processing further includes:

determining an RR interval according to the QRS complex and calculating an estimation value of noise in the RR interval; and determining a detection confidence level of each QRS complex according to the estimation value of the noise and a maximum amplitude in each QRS complex.

Further preferably, the performing interference identification on the heart beat data according to a trained two-class interference identification model includes:

performing cutting and sampling on the heart beat data with a first data amount, and inputting data obtained by the cutting and sampling into the Two-class interference identification model to identify interference;

identifying a data segment with a heart beat interval greater than or equal to a preset interval determination threshold in the heart beat data;

performing a judgment of signal abnormality on the data segment with the heart beat interval greater than or equal to the preset interval determination threshold to determine whether the data segment is an abnormal signal;

if the data segment is not an abnormal signal, according to a set time value, determining a starting data point and an ending data point of sliding sampling in the data segment with a preset time width, and performing the sliding sampling on the data segment from the starting data point until the ending data point to obtain multiple sample data segments; and performing the interference identification on each of the multiple sample data segments.

Further preferably, the inputting the heart beat analysis data of particular heart beats in results of the primary classification information into a trained ST segment and T wave change model for identification, and determining ST segment and T wave evaluation information, includes:

inputting data of the particular heart beats in the primary classification into the trained ST segment and T wave change model according to leads in turn, performing the feature extraction and analysis of the amplitude and time characterization data on the data of the particular heart beats of each lead to obtain ST segment and T wave change information of each lead, and determining the ST segment and T wave evaluation information, which is lead position information that indicates the ST segment and T wave corresponding to heart beat segment data occurs change.

Further preferably, the generating the report graphic data according to typical data segments in each kind of the electrocardiogram event data includes:

performing evaluation on data segments in each kind of electrocardiogram event according to the signal quality evaluation index, and selecting the data segments with the highest signal quality evaluation index as the typical data segments in the electrocardiogram event.

The electrocardiogram information processing method provided by the embodiments of the present disclosure forms the report data through complete and fast automatic analysis of the electrocardiogram data output by the electrocardiogram monitoring device, may query and output the report data according to the requested or set output mode and data format, and supports update and modification of the report data.

A second aspect of embodiments of the present disclosure provides an electrocardiogram workstation, comprising a memory and a processer, the memory is used for storing programs, and the processor is used for executing the first aspect and the methods in implementation manners of the first aspect.

A third aspect of embodiments of the present disclosure provides a computer program product including instructions, when the computer program product runs on a computer, the computer executes the first aspect and the methods in implementation manners of the first aspect.

A fourth aspect of embodiments of the present disclosure provides a computer readable storage medium, the computer readable storage medium stores computer programs, and when the computer programs are executed by the processor, the first aspect and the methods in implementation manners of the first aspect are implemented.

BRIEF DESCRIPTION OF THE DRAWINGS

FIGS. 8a-8g are a report output mode of ambulatory electrocardiogram monitoring data according to an embodiment of the present disclosure.

DETAILED DESCRIPTION

Technical solutions of the present disclosure will be further described in detail below through accompanying drawings and embodiments.

An electrocardiogram workstation sends weak electrocardiogram signals collected from a human body to a computer processing system for amplifying, analyzing and processing, so as to achieve the purpose of electrocardiogram examination and monitoring. The electrocardiogram signals are weak currents reflected by electrical activities of myocardial cells on the body surface, and are recorded by body surface electrodes and an amplification recording system.

The present disclosure performs a complete and rapid automatic analysis based on the recorded electrocardiogram signals to form report data, and establishes a mechanism of querying the report data, outputting according to a requested or set output mode and data format, and updating and modifying the report data.

An electrocardiogram information processing method of the present disclosure will be described in detail below with reference to a flowchart of the electrocardiogram information processing method shown in FIG. 1.

Figure 1:
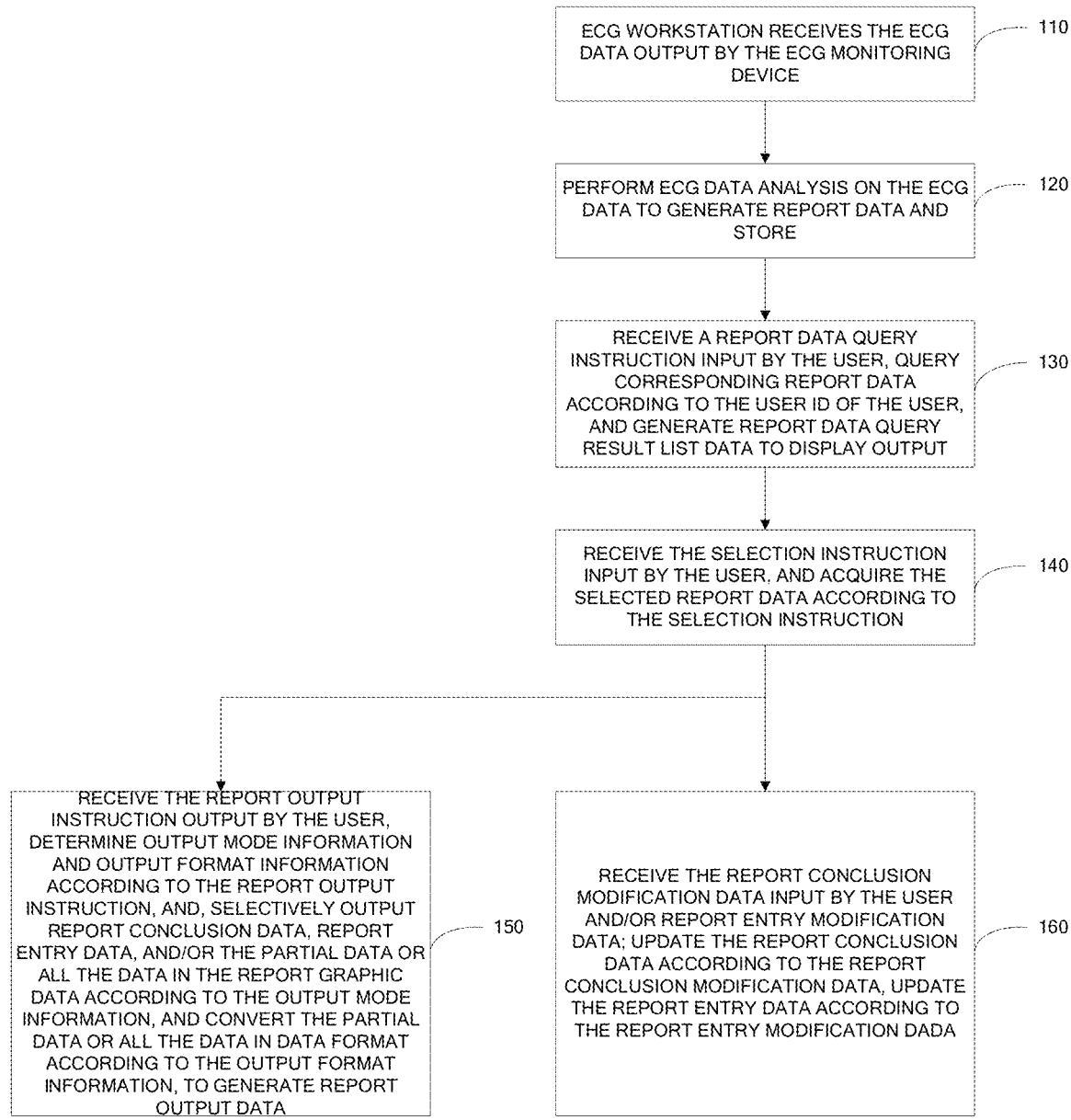
FIG. 1 is a flowchart illustrating an electrocardiogram information processing method according to an embodiment of the present disclosure.

As shown in FIG. 1, the electrocardiogram information processing method of the present disclosure includes the following steps:

Step 110: an electrocardiogram workstation receives electrocardiogram data output by an electrocardiogram monitoring device.

Specifically, the electrocardiogram monitoring device may be single-lead or multi-lead electrocardiogram monitors, and each electrocardiogram monitoring device has a unique device identification (ID), so that measured data may be marked to indicate that the data is obtained by which device.

In the present disclosure, the electrocardiogram workstation refers to a device with an electrocardiogram data analysis and processing function and with the capacity for providing users with information interaction, and it may realize data transmission, user management, data management, report output management of the electrocardiogram data and other functions.

The electrocardiogram workstation may be integrated with the electrocardiogram monitoring device, or the two may be connected through a wired or wireless network for data transmission. The wireless network includes wireless but not limited to wireless local area network based on IEEE 802.11b standard (WIFI), Bluetooth, 3G/4G/5G mobile communication networks, internet of things and other means. The electrocardiogram monitoring device in the embodiment focuses on electrocardiogram signal acquisition, and the output electrocardiogram data is processed by the electrocardiogram workstation.

The electrocardiogram monitoring device collects and records signals generated by electrophysiological activities of heart cells in a single-lead or multi-lead mode through a non-invasive electrocardiogram examination, obtains and sends electrocardiogram data to the electrocardiogram workstation. The electrocardiogram data includes an ID of a tested object, the device ID of the electrocardiogram monitoring device and detection time information.

Step 120: electrocardiogram data analysis is performed on the electrocardiogram data, and the report data is generated and stored.

Considering that other non-cardiogenic electrical signals, such as myoelectric signal interference caused by skeletal muscle activities, are also recorded in the recording process of the electrocardiogram signals, it is thought that effective interference identification and elimination on the electrocardiogram signals are needed to effectively reduce false reports caused by interference signals.

In addition, the electrocardiogram signals are an embodiment of a process of myocardial electrical activities, so the electrocardiogram signals may further reflect a large amount of information about the state of the heart except being used to detect heart rate. When there is a problem with the heart state, the electrocardiogram signals will change accordingly. In the research on existing processing methods of the electrocardiogram signals in the industry, it found that only very limited analysis and alarm have been carried out on the electrocardiogram signals at present. It is thought that improvements may be made from the following points, besides effective interference identification and elimination are taken on the electrocardiogram signals to reduce false positives caused by the interference signals:

First, an accurate identification of P wave and T wave is required in feature extraction of heart beats, which may avoid excessive detection and missed detection in heart beat detection, for example, excessive detection of some special electrocardiogram signals, such as tall T waves of patients with slow heart rhythm or signals with hypertrophy of T wave.

Second, the heart beats should be categorized into more detailed classes, and cannot just be divided in three types of sinus, supraventricular and ventricular, so as to meet complicated and comprehensive analysis requirements of clinical electrocardiogram doctors.

Third, atrial flutter, atrial fibrillation and ST-T changes are correctly identified, which are helpful to assist ST segment and T wave changes on the analysis of myocardial ischemia.

Fourth, an accurate identification of the heart beats and electrocardiogram events.

In the present disclosure, regarding the above points, through analysis and calculation of the electrocardiogram data, especially in the case of the introduction of artificial intelligence (AI) technology, arrhythmia analysis, long intermittent arrest, flutter and fibrillation, conduction block, premature beat and escape beat, bradycardia, tachycardia, ST segment change detection performed on collected digital signals, and analysis and classification of the electrocardiogram events, accurate alarm signals may be achieved, so as to effectively monitor vital signs of patients.

Based on the above points, the processing process of the electrocardiogram data of the present disclosure adopts an artificial intelligence self-learning-based electrocardiogram automatic analysis method, which is realized based on an artificial intelligence Convolutional Neural Network (CNN) model. The CNN model is a supervised learning method in deep learning, which is a multi-layer network (hidden layer) connection structure that simulates a neural network. An input signal sequentially passes through each hidden layer, in which a series of complex mathematical processes (Convolution, Pooling, Regularization, prevention of over-fitting, Dropout, Activation, and general use of Rectified Linear Unit activation function) are carried out. Some features of an object to be identified are automatically abstracted layer by layer, these features are transmitted as input to the higher hidden layers and the last several full connection layers for calculation, and Softmax function is used to perform logistics regression to achieve multi-objective classification.

CNN belongs to the supervised learning method in artificial intelligence. In a training phase, the input signal is processed through multiple hidden layers to reach last full connection layers. There is an error between a classification result obtained by Softmax logical regression and a known classification result (label). One of core ideas of deep learning is to continuously minimize the error through a large number of sample iterations so as to calculate and obtain parameters for connecting neurons in each hidden layer. In this process, it is generally necessary to construct a special cost function, and quickly and effectively updating all connection parameters in a neural network structure with complex depth (number of hidden layers) and breadth (dimension of features) by using a nonlinearly optimized gradient descent algorithm and an error back propagation (BP) algorithm.

In deep learning, data needed to be identified is input into a training model, and finally an identification result is output after the data passes through all layers of the network layers.

In the present disclosure, wave complex feature identification, interference identification, heart beat classification and the like for the electrocardiogram data are all to obtain output results based on trained models of artificial intelligence self-learning, with a fast analysis speed and a high accuracy.

Figure 2:
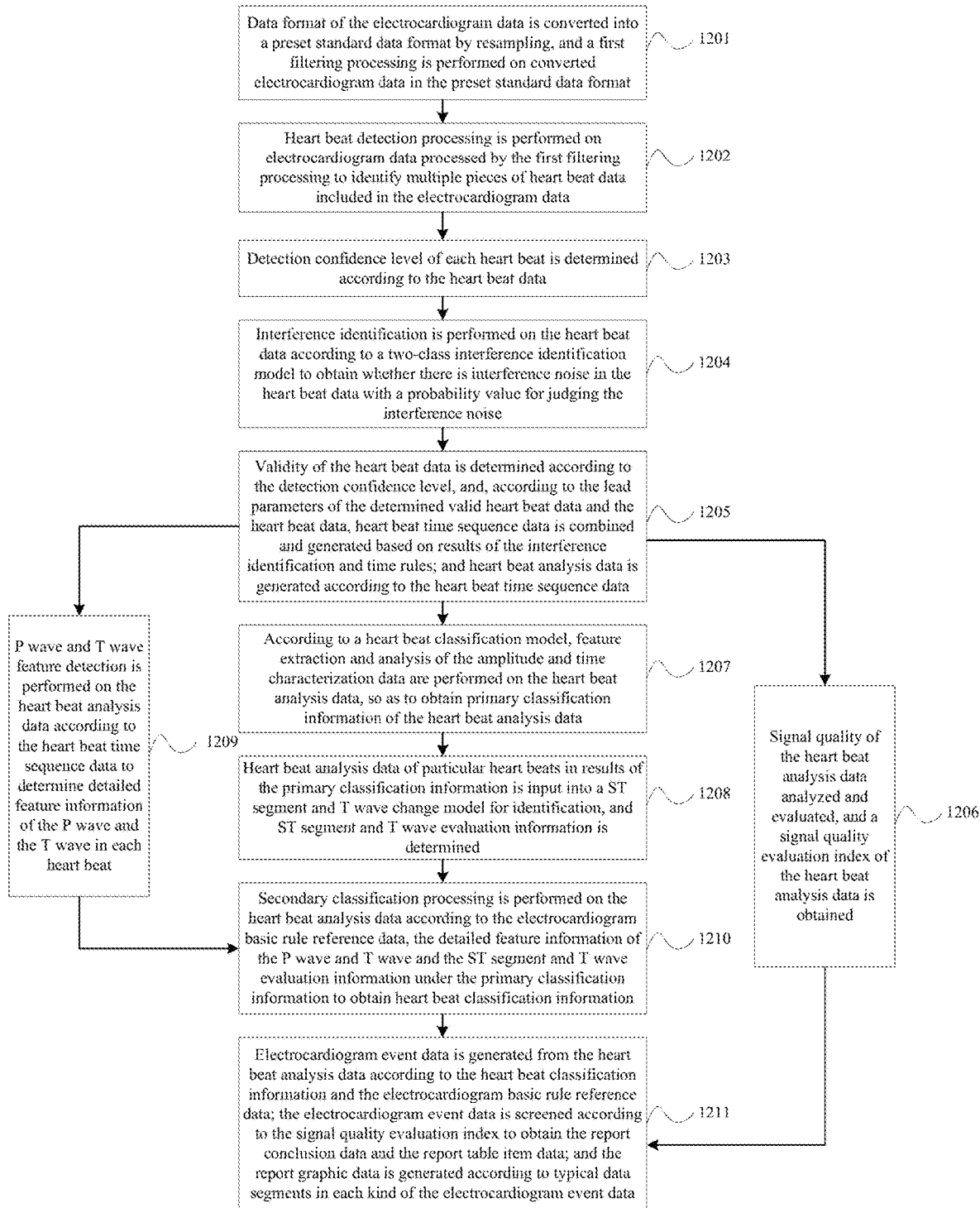
FIG. 2 is a flowchart illustrating a processing method of electrocardiogram data according to an embodiment of the present disclosure.

Specifically, this step is realized through obtaining feature signals of the electrocardiogram data by performing wave complex feature identification on the electrocardiogram data, classifying the electrocardiogram data according to the feature signals, obtaining heart beat classification information combined with electrocardiogram basic rule reference data, generating electrocardiogram event data according to the heart beat classification information, and finally generating the report data. Further, the process may be specifically implemented by the following steps shown in FIG. 2.

Step 1201: a data format of the electrocardiogram data is converted into a preset standard data format by resampling, and a first filtering processing is performed on converted electrocardiogram data in the preset standard data format.

Specifically, the format of the electrocardiogram data is adapted to read, and different readings are implemented for different devices. A baseline needs to be adjusted and the electrocardiogram data needs to be converted into millivolt data according to a gain after reading. Through data resampling, the data is converted into data at a sample frequency that may be processed by the whole process. Then, high frequency, low-frequency noise and baseline drift are eliminated by filtering to improve the accuracy of artificial intelligence analysis. The processed electrocardiogram data is stored in the preset standard data format.

Through this step, differences in the lead, sample frequency and transmission data format used by different electrocardiogram devices may be eliminated, and the high frequency, low-frequency noise and baseline drift may be removed by digital signal filtering.

The digital signal filtering may adopt a high-pass filter, low-pass filter and median filtering, respectively, to eliminate power line noise, electromyogram noise and baseline drift noise, so as to avoid the impact on subsequent analysis.

More specifically, a low-pass, high-pass Butterworth filter may be used for zero-phase shift filtering to eliminate the baseline drift and high-frequency interference, and to retain effective electrocardiogram signals. The median filtering may replace amplitude of a sequence in a center of a window with a median of voltage amplitudes of data points in a sliding window of a preset length of time, and a low-frequency baseline drift may be eliminated.

Step 1202: heart beat detection processing is performed on electrocardiogram data processed by the first filtering processing to identify multiple pieces of heart beat data included in the electrocardiogram data.

Each of the multiple pieces of heart beat data corresponds to a heart beat cycle, including amplitudes and starting-ending time data of corresponding P wave, QRS complex and T wave. The heart beat detection in this step includes two processes: one is signal processing, extracting characteristic frequency bands of the QRS complex from the electrocardiogram data processed by the first filtering processing, and the other is to determine occurrence time of the QRS complex by setting a reasonable threshold. The electrocardiogram normally includes components of P wave, QRS complex and T wave, and a noise component. Generally, the QRS complex has a frequency range of 5 Hz to 20 Hz, so signals of the QRS complex may be extracted by a band-pass filter in this range. However, frequency bands of the P wave, the T wave, and the noise are partially overlapped with the QRS complex, so signals of non QRS complex may not be completely removed by the signal processing. Therefore, it is necessary to extract a position of the QRS complex from a signal envelope by setting a reasonable threshold. The specific detection process is a process based on peak detection. Threshold judgment is sequentially performed for each peak in the signals, and when the threshold is exceeded, a judgment process of the QRS complex is entered to detect more features, such as RR interval, morphology, etc.

During the recording process of the electrocardiogram information, the amplitude and frequency of heart beat signals constantly change, and this characteristic is stronger in a disease state. When the threshold is set, a threshold adjustment needs to be dynamically performed according to the change of data characteristics in the time domain. In order to improve the accuracy and positive rate of the detection, the QRS complex detection is mostly carried out by a double amplitude threshold combined with a time threshold. A high threshold has a high positive rate and a low threshold has a high sensitivity rate. When the RR interval exceeds a certain time threshold, the low threshold is used for detection to reduce missed detection. However, the low threshold is susceptible to T wave and electromyography noise due to its low threshold, which is easy to cause excessive detection. Therefore, the high threshold is preferred for detection.

For heart beat data of different leads, there are lead parameters to characterize, which lead the heart beat data belongs to. Therefore, when the electrocardiogram data is obtained, the information of the lead that the data belongs to may be determined according to a transmission source, and the information is taken as the lead parameters of the heart beat data.

Step 1203: a detection confidence level of each heart beat is determined according to the heart beat data.

Specifically, during the process of the heart beat detection, a confidence calculation module may provide an estimation value of the detection confidence level for the QRS complex according to an amplitude of the QRS complex and an amplitude ratio of noise signals within the RR interval.

Step 1204: interference identification is performed on the heart beat data according to a Two-class interference identification model to obtain whether there is interference in the heart beat data with a probability value for judging the interference.

The long-time recording process is susceptible to interference caused by various influences, resulting in invalid or inaccurate acquired heart beat data, which cannot correctly reflect condition of participants and increases the difficulty and workload of doctors in diagnosis.

In addition, interference data is also a main factor that causes intelligent analysis tools unable to work effectively. Therefore, it is particularly important to minimize external signal interference.

This step is based on an end-to-end two-class identification model with deep learning algorithms as its core, and it has characteristics of high precision and strong generalization performance, and may effectively solve disturbance problems caused by main disturbance sources such as electrode peeling off, exercise interference and electrostatic interference, and thus, the problem of poor identification results caused by various and irregular disturbance data in traditional algorithms is overcome.

Specifically, this may be achieved through the following method:

step A: using the Two-class interference identification model for the heart beat data to identify interference;

step B: identifying a data segment with a heart beat interval greater than or equal to a preset interval determination threshold in the heart beat data;

step C: performing a judgment of signal abnormality on the data segment with the heart beat interval greater than or equal to the preset interval determination threshold to determine whether the data segment is an abnormal signal;

wherein the identification of the abnormal signal includes whether there are electrode peeling off, low voltage, etc.

step D: if the data segment is not an abnormal signal, according to a set time value, a starting data point and an ending data point of sliding sampling in the data segment are determined with a preset time width, and the sliding sampling is performed on the data segment from the starting data point until the ending data point to obtain multiple sample data segments; and step E: performing the process for interference identification on each of the multiple sample data segments.

The above steps A-E will be described in a specific example. The heart beat data of each lead is cut and sampled with a set first data amount, and then input into the Two-class interference identification model, respectively, for classification, and an interference identification result and a probability value corresponding to such result are obtained. For the heart beat data with the heart beat interval greater than or equal to 2 seconds, whether it is signal overflow, low voltage, electrode peeling off is first judged. If it is not in the above case, sliding sampling without overlapping is continuously performed from a left heart beat to the right with the first data amount for identification.

The input may be the first data amount of heart beat data of any lead, the two-class interference identification model is adopted for classification, and a classification result of whether the heart beat data is the interference or not is directly output. The result is obtained quickly, the accuracy is high, the stability performance is good, and effective and high-quality data may be provided for subsequent analysis.

Interference data is often caused by external disturbance factors, mainly including electrode peeling off, low voltage, electrostatic interference and motion interference. Not only interference data generated by different disturbance sources is different, but also interference data generated by a same disturbance source is diverse. At the same time, considering that although the diversity of interference data is widely distributed, the difference between interference data and normal data is very large, so the diversity is ensured as much as possible when collecting interference training data. Furthermore, moving window sliding sampling is adopted to increase the diversity of interference data as much as possible, so as to make the model robust to interference data. Even if interference data in the future is different from any previous interference, with comparison to normal data, its similarity with interference is greater than normal data, thus enhancing the ability of the model to identify interference data.

Figure 3:
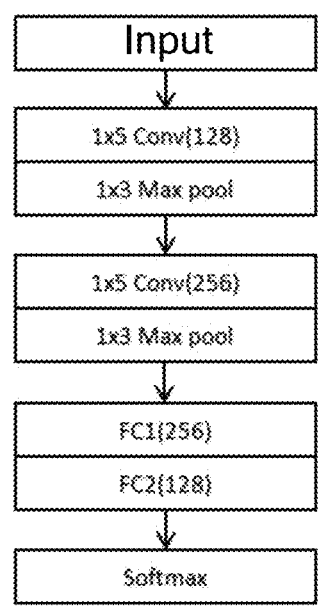
FIG. 3 is a schematic diagram illustrating a two-class interference identification model according to an embodiment of the present disclosure.

The Two-class interference identification model adopted in this step may be shown in FIG. 3. The network first uses two convolutional layers, the convolution kernel in size is 1×5, and each layer is followed by a maximum pooling. The number of the convolution kernel starts from 128, and the number of the convolution kernel doubles every time passing a maximum pooling layer. The convolutional layers are followed by two full connection layers and a Softmax classifier. Since the classification number of the model is two, Softmax has two output units corresponding to categories in turn, and uses cross entropy as the cost function.

For the training of the model, nearly 4 million accurately labeled data segments from 300,000 patients are used. Labeling is divided into two categories: normal electrocardiogram signals or electrocardiogram signal fragments with obvious interference. The segments are labeled by custom-developed tools, and then interference fragment information is saved in a customized standard data format.

In the training process, two GPU servers are used for dozens of round-robin training. In a specific example, for a segment D [300] with a sample rate of 200 Hz and a data length of 300 electrocardiogram voltage values (millivolts), input data is: InputData (i, j), wherein i is a i-th lead, and j is a j-th segment of the i-th lead. All input data is randomly scattered before training, which ensures convergence of the training process. At the same time, collection of too many samples from the electrocardiogram data of a same patient is controlled, improving the generalization ability of the model, that is, an accuracy rate in a real scene. After the training converges, one million pieces of independent test data are used for testing, and the accuracy rate may reach 99.3%. Additionally, specific test data is shown in Table 1 below.

TABLE 1

|  | Interference | Normal |
| --- | --- | --- |
| Sensitivity | 99.14% | 99.32% |
| Positive Predictivity | 96.44% | 99.84% |

Step 1205: a validity of the heart beat data is determined according to the detection confidence level, and, according to the lead parameters of the determined valid heart beat data and the heart beat data, heart beat time sequence data is combined and generated based on results of the interference identification and time rules; and heart beat analysis data is generated according to the heart beat time sequence data.

Specifically, due to the complexity of the electrocardiogram signals and the fact that each lead may be affected by different degrees of interference, there may be excessive detection and missed detection when the heart beat detection depends on a single lead. Time characterization data of heart beat results detected by different leads is not aligned. Therefore, the heart beat data of all leads needs to be combined according to results of the interference identification and time rules to generate complete heart beat time sequence data, and the time characterization data of the heart beat data of all leads is unified. The time characterization data is used to represent time information of each data point on a time axis of electrocardiogram data signals. In the subsequent analysis and calculation, according to the unified heart beat time sequence data, the heart beat data of each lead may be cut with the preset threshold, so as to generate the heart beat analysis data of each lead required for specific analysis.

Before the above mentioned heart beat data of each lead is combined, the validity of the heart beat data needs to be determined according to the detection confidence level obtained in step 1203.

Specifically, the process of combining the heart beat data performed by the lead heart beat combination module is as follows: a time characterization data combination of the heart beat data of different leads is obtained according to a refractory period of electrocardiogram basic rule reference data, the heart beat data with a large deviation is discarded, the time characterization data combination is voted to generate a position of a combined heart beat, and the position of the combined heart beat is added to the combined heart beat time sequence. It returns to a next group of heart beat data to be processed, and repeats until combination of all heart beat data is finished.

The refractory period of the electrocardiogram activities may preferably be between 200 ms and 280 ms. The time characterization data combination of the heart beat data of different leads obtained should meet the following conditions: each lead in the time characterization data combination of the heart beat data includes at most the time characterization data of one piece of heart beat data. When the time characterization data combination of the heart beat data is voted on, it is determined by a percentage of a number of leads with detected heart beat data in a number of effective leads. If a position of the time characterization data of the heart beat data corresponding to a lead is a low voltage segment, an interference segment or electrode peeling off, the lead is considered as an invalid lead for the heart beat data. The specific position of the combined heart beat may be calculated and obtained by using an average value of the time characterization data of the heart beat data. During the combining process, the refractory period is set in this method to avoid erroneous combining.

In this step, the unified heart beat time sequence data is output through combining. This step may simultaneously lower excessive detection and missed detection rates of the heart beat, and effectively improve the sensitivity and positive predictivity of the heart beat detection.

Step 1206: a signal quality of the heart beat analysis data is analyzed and evaluated, and a signal quality evaluation index of the heart beat analysis data is obtained.

If the monitored electrocardiogram data is resting electrocardiogram data, the signal quality is relatively good, and the proportion of valid signals is relatively high. In this case, signal quality evaluation may be avoided. If the monitored data is ambulatory electrocardiogram data, various disturbances will occur during the monitoring process, resulting in relatively many invalid signals. In order to prevent invalid signals from affecting the final result calculation, the signal quality evaluation needs to be performed to reduce the impact of the invalid signals on the final result.

Specifically, the signal quality evaluation index is determined by extracting RR interval signals in the heart beat analysis data, performing second filtering processing and envelope calculation on the RR interval signals to determine a signal intensity of the noise, and calculating a signal-to-noise ratio of a maximum amplitude of corresponding heart beat time sequence data. The following steps may be included:

step A: position information and width information of the QRS complex in the heart beat analysis data are extracted;

step B: RR interval signals within RR interval between two adjacent QRS complex signals are extracted;

step C: filtering the RR interval signals is performed, and an envelope calculation is performed on filtered signals to obtain an average power of noise signals in the RR interval; wherein the average power of the noise signals in the RR interval is an average of an envelope amplitude in the RR interval; and step D: the signal quality evaluation index is obtained according to the average power of the noise signals and a power of the signals of the QRS complex.

Further, the signal quality evaluation index may be expressed by a noise level in the RR interval respect to the QRS complex, and specifically, it is calculated based on the power of the QRS complex and the average power of the noise signals.

The signal quality evaluation index is expressed by the formula:

$$SNR(i) = \frac{S_i}{\sum N_{i,t} \div T};$$

wherein $S_i$ is an amplitude of a i-th QRS complex, $N_{i,t}$ is an amplitude of a t-th sample point in a i-th RR interval, and T is a length of the RR interval.

Step 1207: according to a heart beat classification model, feature extraction and analysis of the amplitude and time characterization data are performed on the heart beat analysis data, so as to obtain primary classification information of the heart beat analysis data.

Specifically, this step is performed after step 1205. Since there are differences in signal measurement, acquisition, output lead data and other aspects for different electrocardiogram monitoring devices, a simple single-lead classification method or a multi-lead classification method may be adopted according to specific situations. The multi-lead classification method includes lead voting decision classification method and lead synchronous correlation classification method. The lead voting decision classification method is a voting decision method that leads are independently classified based on the heart beat analysis data of each lead, and then voting results are merged to determine a classification result. The lead synchronous correlation classification method is a method for synchronous correlation and analysis of the heart beat analysis data of each lead. The single-lead classification method is to directly use a corresponding lead model to classify the heart beat analysis data of a single-lead device, and there is no voting decision process. The classification methods mentioned-above will be, respectively, described in the following.

The single-lead classification method includes:

according to the heart beat time sequence data, cutting is performed on the heart beat data of the single lead to generate the heart beat analysis data of the single lead, and the heart beat analysis data of the single lead is input into the trained heart beat classification model corresponding to such lead for the feature extraction and analysis of the amplitude and time characterization data, so as to obtain the primary classification information of the single lead.

The lead voting decision classification method may include:

firstly, according to the heart beat time sequence data, cutting is performed on the heart beat data of each lead to generate the heart beat analysis data of each lead;

secondly, according to the trained heart beat classification model corresponding to each lead, the feature extraction and analysis of the amplitude and time characterization data are performed on the heart beat analysis data of each lead, so as to obtain classification information of each lead; and thirdly, classification voting decision calculation is performed according to the classification information of each lead and lead weight reference coefficients, so as to obtain the primary classification information. Specifically, the lead weight reference coefficients are voting weight coefficients of each lead for different heart beat classifications based on the Bayesian statistical analysis of the electrocardiogram data.

The lead synchronous correlation classification method may include:

according to the heart beat time sequence data, cutting is performed on the heart beat data of each lead to generate the heart beat analysis data of each lead; and then, according to a trained multi-lead synchronous correlation classification model, the feature extraction and analysis of a synchronous amplitude and time characterization data are performed on the heart beat analysis data of each lead, so as to obtain the primary classification information of the heart beat analysis data.

An input of the synchronous correlation classification method of the heart beat data is data of all leads of the ambulatory electrocardiogram device, and data points with a same position and a certain length of each lead are intercepted according to unified heart beat positions of the heart beat analysis data, and are synchronously delivered to a trained artificial intelligence deep learning model for calculation and analysis, and an output is an accurate heart beat classification in which electrocardiogram signal characteristics of all lead and heart rhythm characteristics correlated with the heart beat in time are comprehensively considered at each heart beat position.

This method fully considers the data of different leads of the electrocardiogram is, actually measuring information flow of heart electrical signals transmitted in the directions of different electrocardiogram axis vectors, and multi-dimensional digital characteristics transmitted by the electrocardiogram signal in time and space are comprehensively analyzed, so it effectively overcomes the defect that the traditional method only relies on independent analyses of a single lead, and then results are accumulated to conduct some statistical voting methods through which classification errors are easily obtained, and greatly improves the accuracy of the heart beat classification.

Figure 4:
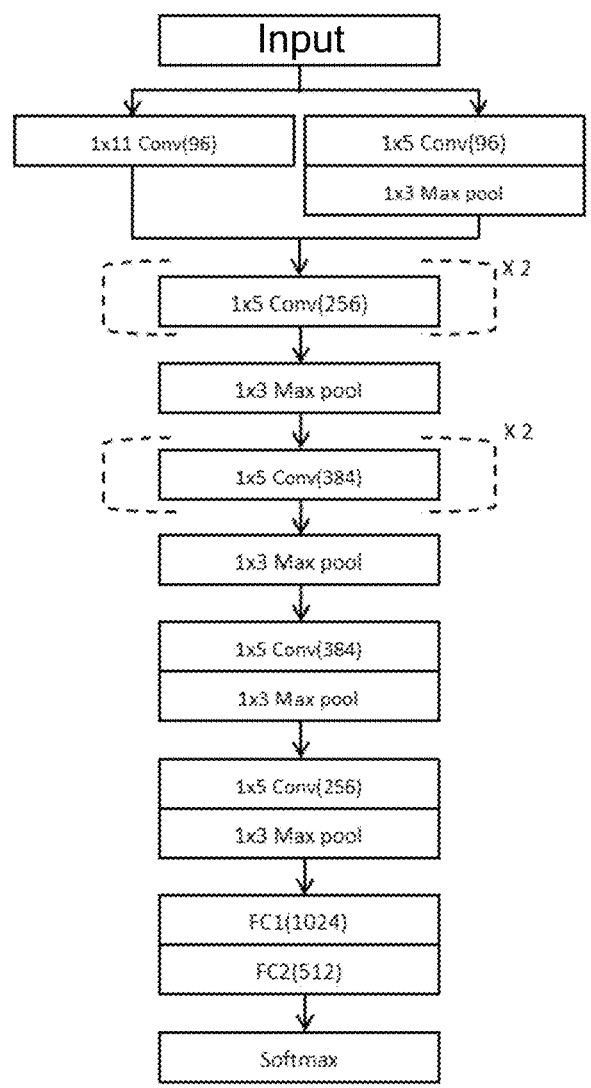
FIG. 4 is a schematic diagram illustrating a heart beat classification model according to an embodiment of the present disclosure.

The heart beat classification model adopted in this step may be shown in FIG. 4, which specifically may be an end-to-end multi-label classification model inspired by CNN models based on artificial intelligence deep learning such as AlexNet, VGG16, Inception. Specifically, the network of this model is a seven-layer convolution network, and each convolution is followed by an activation function. A first layer is a convolution layer having two different scales, followed by six convolution layers. The number of convolution kernels of the seven-layer convolution are 96, 256, 256, 384, 384, 384 and 256, respectively. Except for the convolution kernel of the first layer, which has two scales of 5 and 11, the convolution kernels of other layers have a scale of 5. Third, fifth, sixth and seventh convolution layers are followed by a pooling layer. Finally, two full connection layers follow.

The heart beat classification model in this step is obtained by training 17 million data samples of 300,000 patients in a training set. These samples are generated by accurately labeling the data according to requirements of ambulatory electrocardiogram analysis and diagnosis. Labeling is mainly for common arrhythmias, conduction block, ST segment and T wave changes, which may meet model training in different application scenes. Specifically, labeled information is stored in a preset standard data format. In the preprocessing of training data, in order to increase the generalization ability of the model, small sliding is made for a classification with a small sample size to expand the data. Specifically, the data is moved 2 times based on each heart beat according to a certain step (such as 10-50 data points), so that the data may be increased by 2 times, and the recognition accuracy of classification samples with a small amount of data is improved. The generalization ability has also been verified to be improved from the actual result.

In an actual training process, two GPU servers are used for dozens of round-robin training. After the training converges, 5 million pieces of independent test data are used for testing, and the accuracy rate may reach 91.92%.

An interception length of the training data may be from 1 second to 10 seconds. For example, a sample rate is 200 Hz, a sample length is 2.5 s, an obtained data length is a segment D[500] of 500 electrocardiogram voltage values (millivolts), and input data is: InputData (i, j), wherein i is a i-th lead, and j is a j-th segment of the i-th lead. All input data is randomly scattered before training, which ensures convergence of the training process. At the same time, collection of too many samples from the electrocardiogram data of a same patient is limited, which improves the generalization ability of the model, that is, an accuracy rate in a real scene. During the training, segment data D corresponding to all leads is synchronously input, and lead data of multiple spatial dimensions (different electrocardiogram axis vectors) of each time position is synchronously learned according to a multi-channel analysis method of image analysis, so that a more accurate classification result than a conventional algorithm is obtained.

Step 1208: the heart beat analysis data of particular heart beats in results of the primary classification information is input into a ST segment and T wave change model for identification, and ST segment and T wave evaluation information is determined.

The ST segment and T wave evaluation information is lead position information that the ST segment and T wave corresponding to the heart beat analysis data is changed. In clinical diagnosis, changes for the ST segment and T wave are required to be located to a specific lead.

Wherein, the data of the particular heart beats of the primary classification information refers to the heart beat analysis data including sinus heart beat (N) and other heart beat types that may include ST segment changes.

The data of particular heart beats in the primary classification information is put into a trained artificial intelligence deep learning model for identifying the ST segment and T wave changes according to each lead in turn by a ST segment and T wave change lead location module, and calculation and analysis is performed. An output result indicates whether features of lead segments conform to the conclusion that ST segment and T wave change, so that the information of leads where the ST segment and T wave changes occur may be determined, that is, the ST segment and T wave evaluation information. The specific method may be as follows: the heart beat analysis data of each lead that the results in the primary classification information is the sinus heart beat is put into the ST segment and T wave change model, and the sinus heart beat data is identified and judged one by one, so as to determine whether the sinus heart beat has characteristics of ST segment and T wave change and specific lead position information that the change occurs, and the ST segment and T wave evaluation information is determined.

Figure 5:
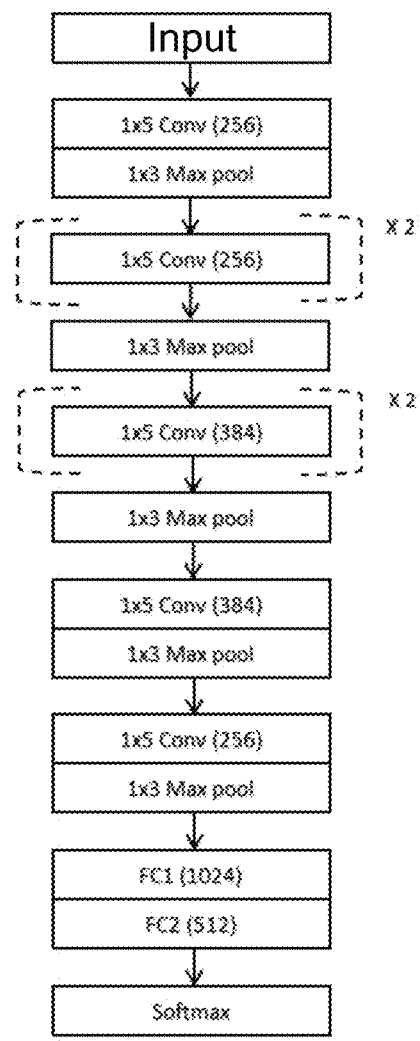
FIG. 5 is a schematic diagram illustrating a ST segment and T wave change model according to an embodiment of the present disclosure.

The ST segment and T wave change model adopted in this step may be as shown in FIG. 5, and it may be an end-to-end classification model inspired by CNN models based on artificial intelligence deep learning such as AlexNet and VGG16. Specifically, the model is a seven-layer network, which includes seven layers of convolution, five layers of pooling and two layers of full connection. A convolution kernel used in all layers of convolution is 1×5, and the number of filters for each layer of the convolution is different. The number of the filters for a first layer of convolution is 96; a second layer of convolution and a third layer of convolution are used together, and the number of the filters is 256; a fourth layer of convolution and a fifth layer of convolution are used together, and the number of the filters is 384; the number of the filters for a sixth layer of convolution is 384; the number of the filters for a seventh layer of convolution is 256. The first, third, fifth, sixth and seventh layers of convolution are followed by the layers of pooling, and then, the two layers of full connection follow. Finally, a Softmax classifier is used to divide the results into two categories. In order to increase the nonlinearity of the model and extract the features of high dimensions of the data, the mode that two layers of convolution are used together is adopted.

Since a proportion of the heart beat with the ST segment and T wave changes in all heart beats is relatively low, in order to take into account a diversity of the training data and a balance of the amount of data in each category, a ratio of training data without ST segment and T wave changes and with ST segment and T wave changes is selected about 2:1, which ensures the good generalization ability of the model in the process of classification and avoid to appear a tendency of a category accounting for a relatively large proportion in the training data. Forms of the heart beat are diverse and different individuals show different forms, therefore, in order to make the model estimate distribution of each classification well and extract features effectively, training samples are collected from individuals of different ages, weights, genders and residential areas. In addition, since the electrocardiogram data of a single individual in a same time period is often highly similar, in order to avoid over-fitting, when acquiring the data of the single individual, a small number of samples in different time periods are randomly selected from all the data. Finally, due to characteristics that the forms of the heart beat of patients have large differences between individuals and high similarity within the individual, different patients are divided into different data sets when dividing training sets and test sets, so as to prevent the data of a same individual from appearing in the training sets and test sets at the same time. Therefore, test results of the obtained model are closest to real application scenes, ensuring the reliability and universality of the model.

Step 1209: P wave and T wave feature detection is performed on the heart beat analysis data according to the heart beat time sequence data to determine detailed feature information of the P wave and the T wave in each heart beat.

Specifically, the detailed feature information includes data of amplitudes, directions, forms and starting-ending time. In the analysis of the heart beat signals, the features of the P wave, T wave and QRS complex are also important basis for the electrocardiogram analysis.

In the P wave and T wave feature detection module, the features of the P wave, T wave, and QRS complex are extracted by calculating a position of a segmentation point of the QRS complex and a position of a segmentation point of the P wave and the T wave, which may be realized by QRS complex segmentation point detection, single-lead PT detection algorithms and multi-lead PT detection algorithms, respectively.

The QRS complex segmentation point detection: according to a segment power maximum point and starting and ending points of the QRS complex provided by QRS complex detection algorithms, a R point, R' point, S point and S' point of the QRS complex in a single lead are searched. When there is multi-lead data, a median of each segmentation point is calculated as the final position of the segmentation point.

The single-lead P wave and T wave detection algorithms: compared with the QRS complex, the P wave and T wave are relatively low in amplitude and gentle in signal, and easy to be submerged in the low-frequency noise, which is difficult in the detection. In this method, according to a result of the QRS complex detection, third filtering is performed on the signals by using a low-pass filter to increase relative amplitudes of the P and T waves after eliminating an influence of the QRS complex on low-frequency bands. The T wave is then searched between two QRS complexes by the peak detection. Since the T wave is a wave complex generated by ventricular repolarization, there is a definite time-locked relationship between the T wave and the QRS complex. Based on the detected QRS complex, a midpoint between each QRS complex and next QRS complex (e.g., limited to a range from 400 ms to 600 ms after a first QRS complex) is taken as an ending point of the T wave detection, and the largest peak in this range is taken as the T wave. Then a peak with the largest amplitude in remaining peaks is selected as the P wave. At the same time, direction and morphology features of the P wave and the T wave are determined according to peak values and position data of the P wave and the T wave. Preferably, a cut-off frequency of the low-pass filtering is set from 10 Hz to 30 Hz.

The multi-lead P wave and T wave detection algorithms: in the case of multiple leads, each wave in a heart beat is generated at same time, but has different space distribution, while the noise has different time and space distribution, therefore the P and T waves may be detected by tracing algorithms. Firstly, QRS complex elimination processing is performed on the signals and third filtering is performed on the signals by using a low-pass filter to remove interference, and then individual independent components of an original waveform are calculated by an independent component analysis algorithm. In separated individual independent components, corresponding components are selected as P wave and T wave signals according to distribution characteristics of peaks and the position of the QRS complex, and the direction and morphology features of the P wave and the T wave are determined.

Step 1210: secondary classification processing is performed on the heart beat analysis data according to the electrocardiogram basic rule reference data, the detailed feature information of the P wave and T wave and the ST segment and T wave evaluation information under the primary classification information to obtain heart beat classification information.

Specifically, the electrocardiogram basic rule reference data is generated according to the description of basic rules of cardiomyocytes electrophysiological activities and electrocardiogram clinical diagnosis in authoritative electrocardiogram textbooks, such as a minimum time interval between two heart beats, a minimum interval between the P wave and R wave. The primary classification information after classification of the heart beat is subdivided, is mainly based on the RR interval between the heart beats and a medical significance of different heart beat signals on each lead. According to the electrocardiogram basic rule reference data combined with classification and identification of a certain number of continuous heart beats and the detailed feature information of the P wave and T wave, a class of ventricular heart beats is divided into more detailed heart beat classes by the heart beat verification module, including ventricular premature beat (V), ventricular escape beat (VE), ventricular tachycardia premature beat (VT), and supraventricular heart beats are subdivided into supraventricular premature beat (S), atrial escape beat (SE), junctional escape beat (JE) and atrial tachycardia premature beat (AT), etc.

In addition, through the secondary classification processing, erroneous classification identification that does not conform to the electrocardiogram basic rule reference data in the primary classification may also be corrected. The subdivided heart beat classifications are pattern matched according to the electrocardiogram basic rule reference data, classification identification, which does not conform to the electrocardiogram basic rule reference data is found, and corrected to a reasonable classification according to the RR interval and classification labels before and after.

Specifically, after the secondary classification processing, a variety of heart beat classifications may be output, such as: normal sinus heart beat (N), complete right bundle branch block (N_CRB), complete left bundle branch block (N_CLB), intraventricular block (N_VB), first degree atrioventricular block (N_B1), pre-excitation (N_PS), ventricular premature beat (V), ventricular escape beat (VE), ventricular tachycardia premature beat (VT), supraventricular premature beat (S), atrial escape beat (SE), junctional escape beat (JE), atrial tachycardia premature beat (AT), atrial flutter/atrial fibrillation (AF) and artifact (A).

The calculation of basic heart rate parameters may also be completed through this step. The calculated basic heart rate parameters include the RR interval, heart rate, QT time, QTc time and other parameters.

Then, according to results of the secondary classification of the heart beats, pattern matching is performed according to the electrocardiogram basic rule reference data, and the following typical electrocardiogram events corresponding to the electrocardiogram event data may be obtained, including but not limited to:

supraventricular premature beat
pairs of supraventricular premature beat
supraventricular premature beat bigeminy
supraventricular premature beat trigeminy
atrial escape beat
atrial escape rhythm
junctional escape beat
junctional escape rhythm
non-paroxysmal supraventricular tachycardia
fastest supraventricular tachycardia
longest supraventricular tachycardia
supraventricular tachycardia
short supraventricular tachycardia
atrial flutter-atrial fibrillation
ventricular premature beat
pairs of ventricular premature beat
ventricular premature beat bigeminy
ventricular premature beat trigeminy
ventricular escape beat
ventricular escape rhythm
accelerated idioventricular rhythm
fastest ventricular tachycardia
longest ventricular tachycardia
ventricular tachycardia
short ventricular tachycardia
second-degree type I sinoatrial block
second-degree type II sinoatrial block
first-degree atrioventricular block
second-degree type I atrioventricular block
second-degree type II atrioventricular block
second-degree type II (2:1) atrioventricular block
high-degree atrioventricular block
complete left bundle branch block
complete right bundle branch block
intraventricular block
pre-excitation syndrome
ST segment and T wave change
longest RR interval Step 1211: the electrocardiogram event data is generated from the heart beat analysis data according to the heart beat classification information and the electrocardiogram basic rule reference data; the electrocardiogram event data is screened according to the signal quality evaluation index to obtain the report conclusion data and the report table item data; and the report graphic data is generated according to typical data segments in each kind of the electrocardiogram event data.

According to the signal quality evaluation index, untrusted events are removed from the electrocardiogram event data, various heart rate parameters are calculated, the number, occurrence time of events are counted, and the report conclusion data and the report table item data are obtained.

Specifically, the calculation of the heart rate parameters includes calculation of an average heart rate, a maximum heart rate and a minimum heart rate, etc. When calculating the maximum and minimum heart rates, a fixed-length segment is taken as a statistical unit, and whole process scanning and statistical comparison are performed on the heart beats one by one. The length of the segment is generally 8-10 seconds, and it may be freely set as required. When calculating the heart rate, different statistical calculation methods for heart beat types are adopted for electrocardiogram dominated by sinus heart rate and electrocardiogram dominated by ectopic heart rate. When calculating the maximum and minimum heart rates, only the sinus heart beat is calculated for the electrocardiogram dominated by sinus heart rate. For electrocardiogram dominated by the atrial flutter/atrial fibrillation, only the atrial flutter/atrial fibrillation and sinus heart beats are calculated. For electrocardiogram dominated by other non atrial flutter/atrial fibrillation ectopic heart beats, all types of heart beats except the artifact are involved in the calculation.

Quality evaluation is performed on the electrocardiogram event data according to the signal quality evaluation index, event segments with the highest data signal quality are selected, meanwhile, a number of event types included in the segments is analyzed, the most representative segment is preferentially selected, a starting position of the segment is preferred to ensure that an event heart beat is located in a middle of the selected segment as far as possible, and the report graphic data is generated.

In a preferred embodiment, selection rules of the electrocardiogram events may be specifically described as follows.

A single segment is selected for general electrocardiogram events. When the heart rate of a first heart beat of the segment is greater than or equal to 100, a distance from a starting point of the segment to the first heart beat is 0.3 seconds. When the heart rate of the first heart beat of the segment is less than or equal to 45, the distance from the starting point of the segment to the first heart beat is 0.37 seconds.

For electrocardiogram events with multiple segments, it is necessary to perform quality evaluation on the multiple segments, and calculate a proportion of non-interference signals of intercepted segments according to the signal quality evaluation index. When the proportion of the non-interference signals reaches a set threshold (preferably, the threshold is determined in a range of 60%-95%), the segments meet screening conditions, from which an optimal typical data segment is obtained.

According to the ID of the tested object, the report conclusion data, the report table item data and the report graphic data are associated and stored as the report data. Therefore, various report data related to the ID of the tested object may be directly obtained according to such ID of the tested object when querying and calling. The report data also correspondingly includes the detection time information of the report data. This information should include at least information of acquisition time/period of the electrocardiogram data, and may also include the time when the report data is last updated. Such time may also be recorded because of possible modifications to the report data.

Step 130: a report data query instruction input by a user is received, corresponding report data is queried according to a user ID of the user, and report data query result list data is generated and displayed.

Specifically, the electrocardiogram workstation may provide the user with a human-computer interaction interface through which the user may log in and query the report data.

When the user logs in, the electrocardiogram workstation performs permission verification according to login information of the user, and performs data query authority management according to the user ID corresponding to user authority information to obtain the corresponding report data. Then data is extracted from the report data to obtain the report data query result list data for output. The report data query result list data includes at least the ID of the tested object and the detection time information of one or more pieces of report data obtained by the querying.

The following will be described with specific examples, which are only examples and do not limit the specific implementation.

For example, the user is an attending doctor of a certain department. After logging in to the electrocardiogram workstation, when querying the report data of a patient, the electrocardiogram workstation obtains IDs of patients of the department according to the authority of the doctor, queries and matches IDs of all tested objects according to the ID of the patient, and obtains the report data, preferably the report data within a set period of time, of the patient that the attending doctor has authority to consult. Then, the data is extracted from the report data, and at least the ID of the tested object and the detection time information are extracted to generate the report data query result list data, which is preferably displayed on the human-computer interaction interface of the electrocardiogram workstation in a list manner. Wherein, the identification ID of the tested objects may be a name or patient file number, etc. The display order of the list may be arranged in the order of the IDs of the tested objects, or in the order/reverse order of the detection time information.

For another example, if the user is a patient, after logging in to the electrocardiogram workstation and querying the report data of the patient, the electrocardiogram workstation obtains all or a set period of report data related to the ID of the patient according to the authority of the patient. Similarly, the data is extracted from the report data, at least the ID of the tested object and the detection time information are extracted, and the report data query result list data is generated and displayed on the human-computer interaction interface of the electrocardiogram workstation in the list manner.

Step 140: a selection instruction input by the user is received, and selected report data is acquired according to the selection instruction.

Specifically, the user makes selection input through the human-computer interaction interface, thereby determining the report data to be selected.

A single processing operation or batch processing operation on the report data is supported based on different operation purposes.

For example, the report data needs to be output, viewed, edited and modified. A single query result may be selected from the report data query result list data to obtain one report data.

If the report data is printed, transmitted or downloaded, multiple query results may be simultaneously selected from the report data query result list data to obtain multiple pieces of report data at one time, which may simplify the operation.

Through the electrocardiogram workstation, users may be performed operation authority management. For example, user category information of the users may be set, such as doctors, ordinary staff, patients, etc., and the authority of different categories of users is set to be different. For example, if the user category information is a doctor, the report data may be queried, modified, downloaded, and forwarded. If the user category information is an ordinary staff member or a patient, the report data may only be queried and printed.

After selecting the report data, operations such as output (step 150 below), modification (step 160 below) and the like may be performed on the report data.

Step 150: a report output instruction input by the user is received, output mode information and output format information are determined according to the report output instruction, part or all of data in the report conclusion data, the report table item data and/or the report graphic data is selectively output according to the output mode information, and data format conversion is performed on the part or all of the data according to the output format information to generate report output data.

When the user selects the report data from the report data query result list data and requests to output the report data, the electrocardiogram workstation acquires selected report data according to the selection instruction from the user, and generates the report output data according to the report output mode information and the report output format information accordingly.

Figure 7A:
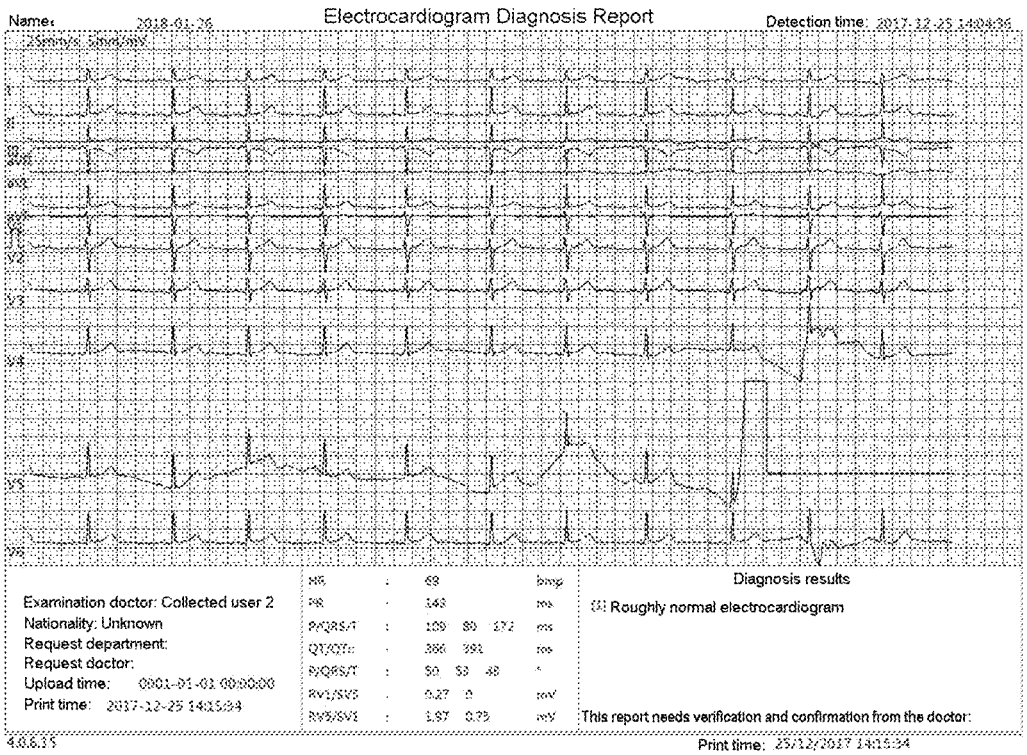
FIGS. 7a-7c are a report output mode of resting electrocardiogram monitoring data according to an embodiment of the present disclosure.
Figure 7B:
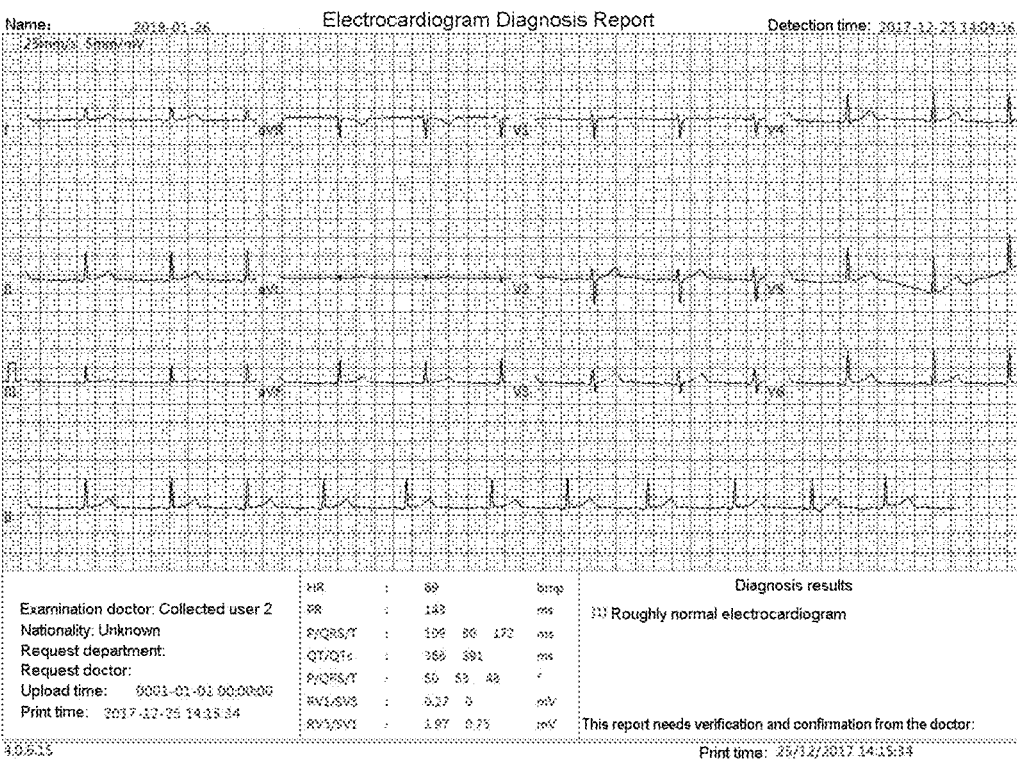
Figure 7C:
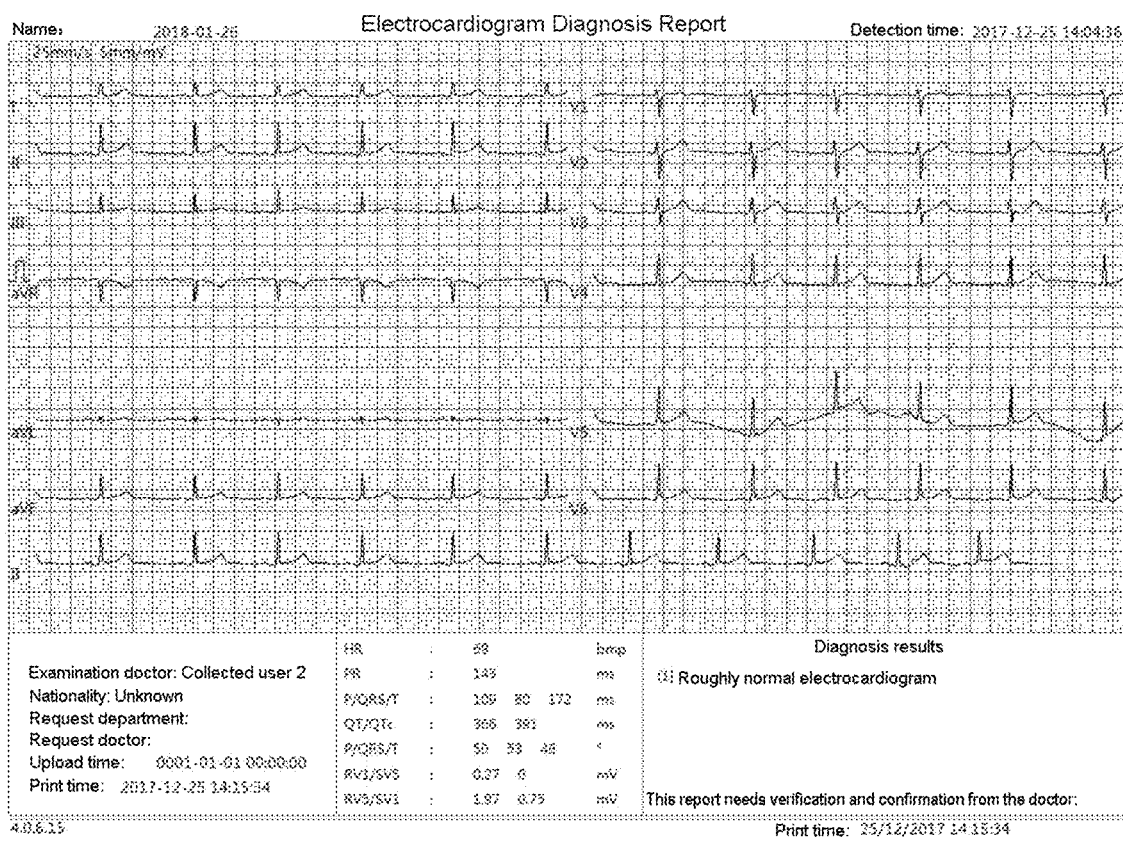
Figure 8B:
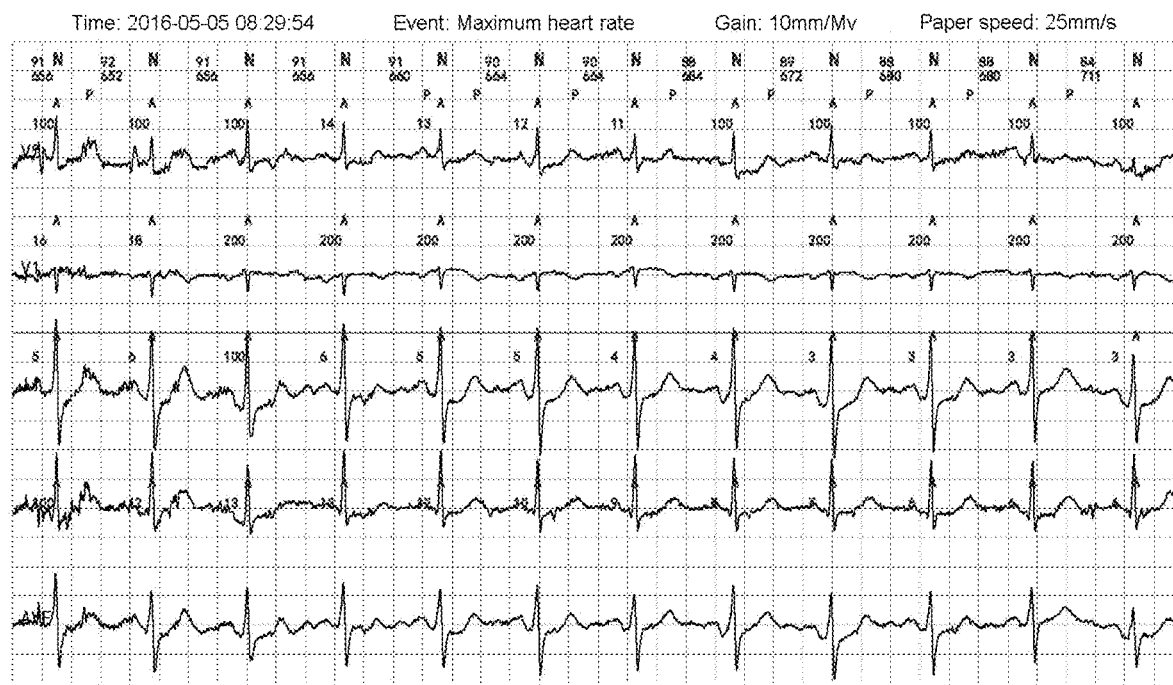
Figure 8B:
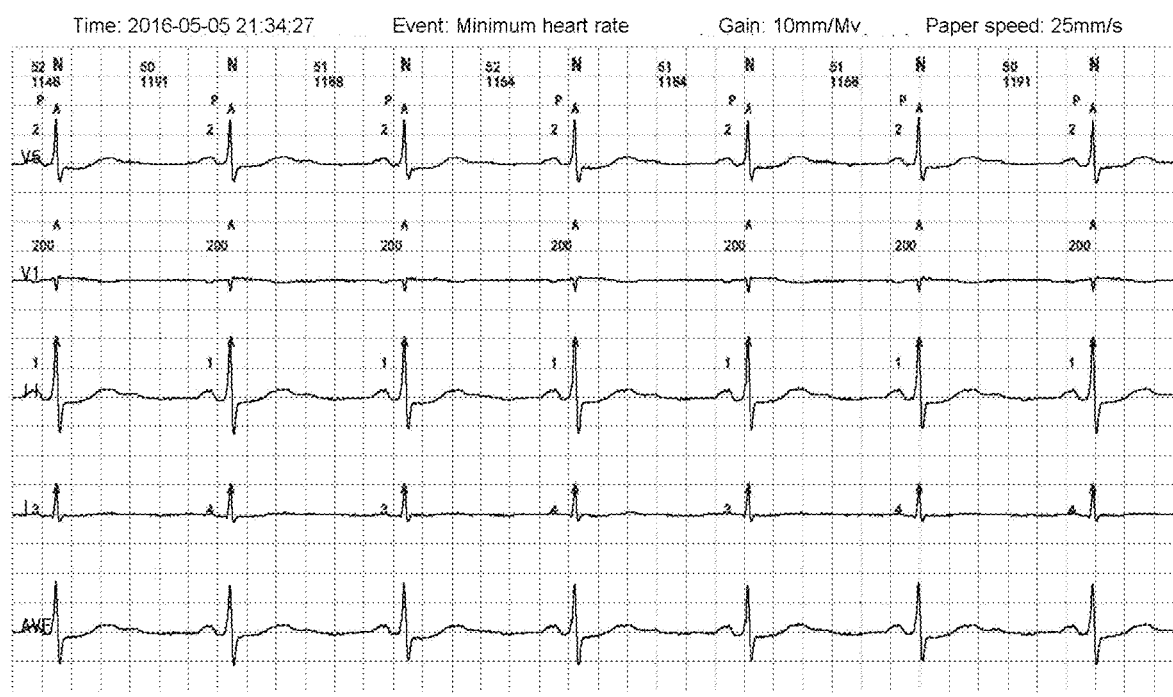
Figure 8C:
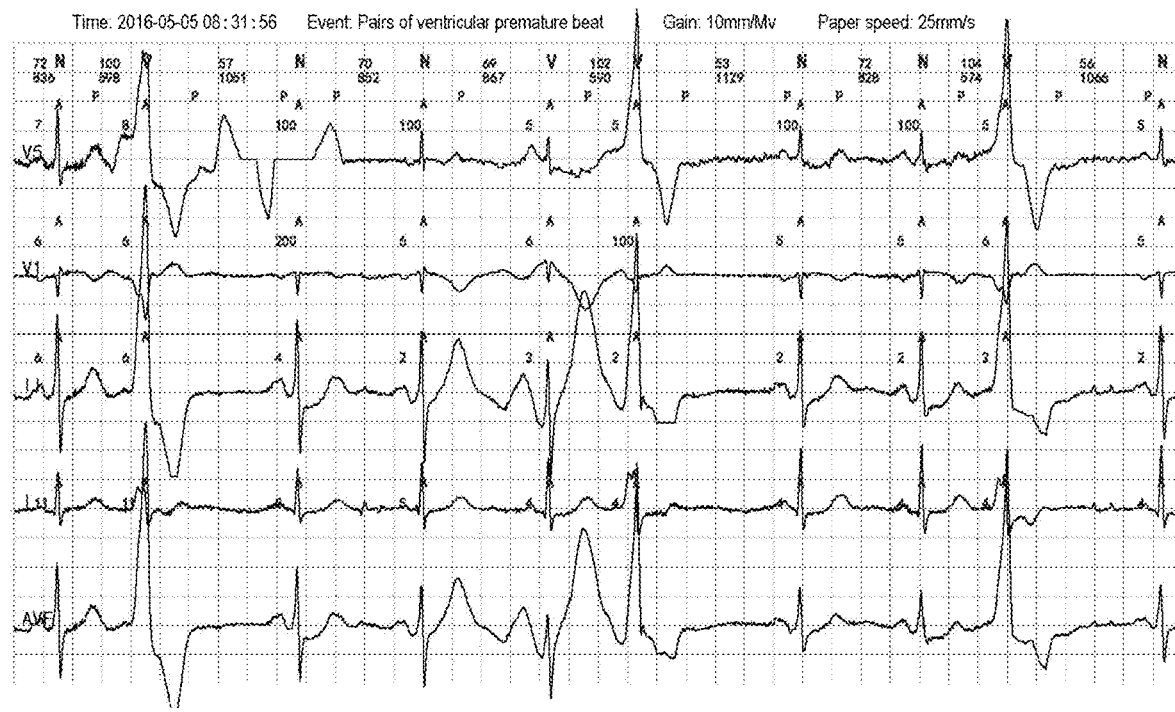
Figure 8C:
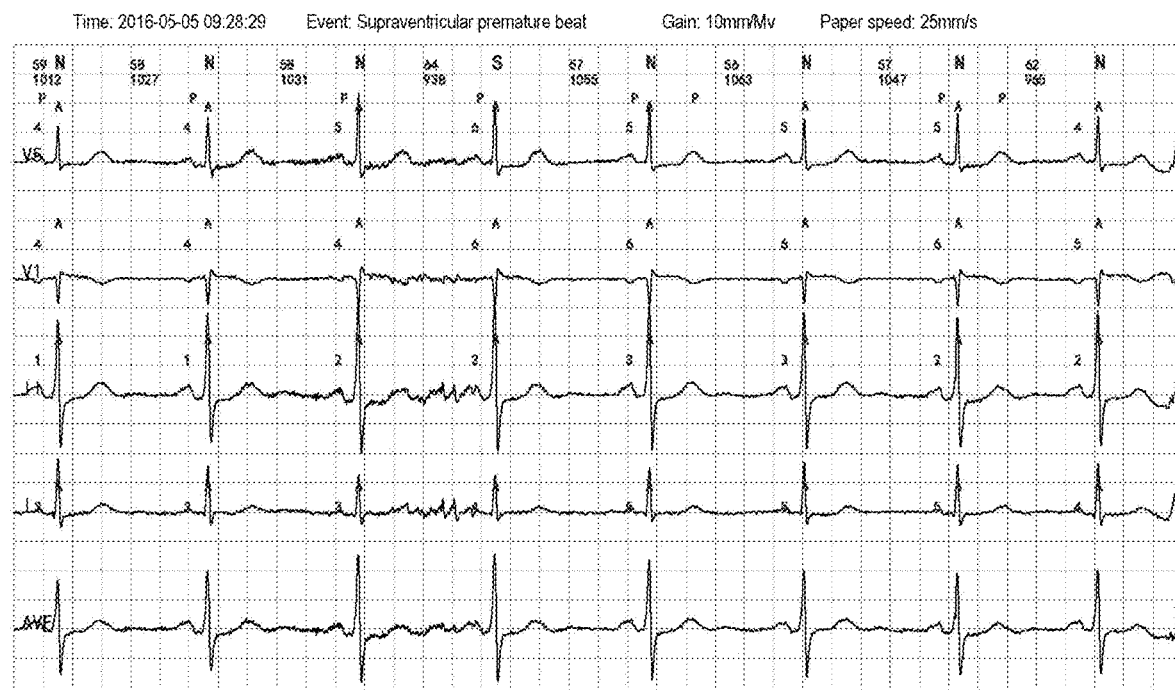
Figure 8D:
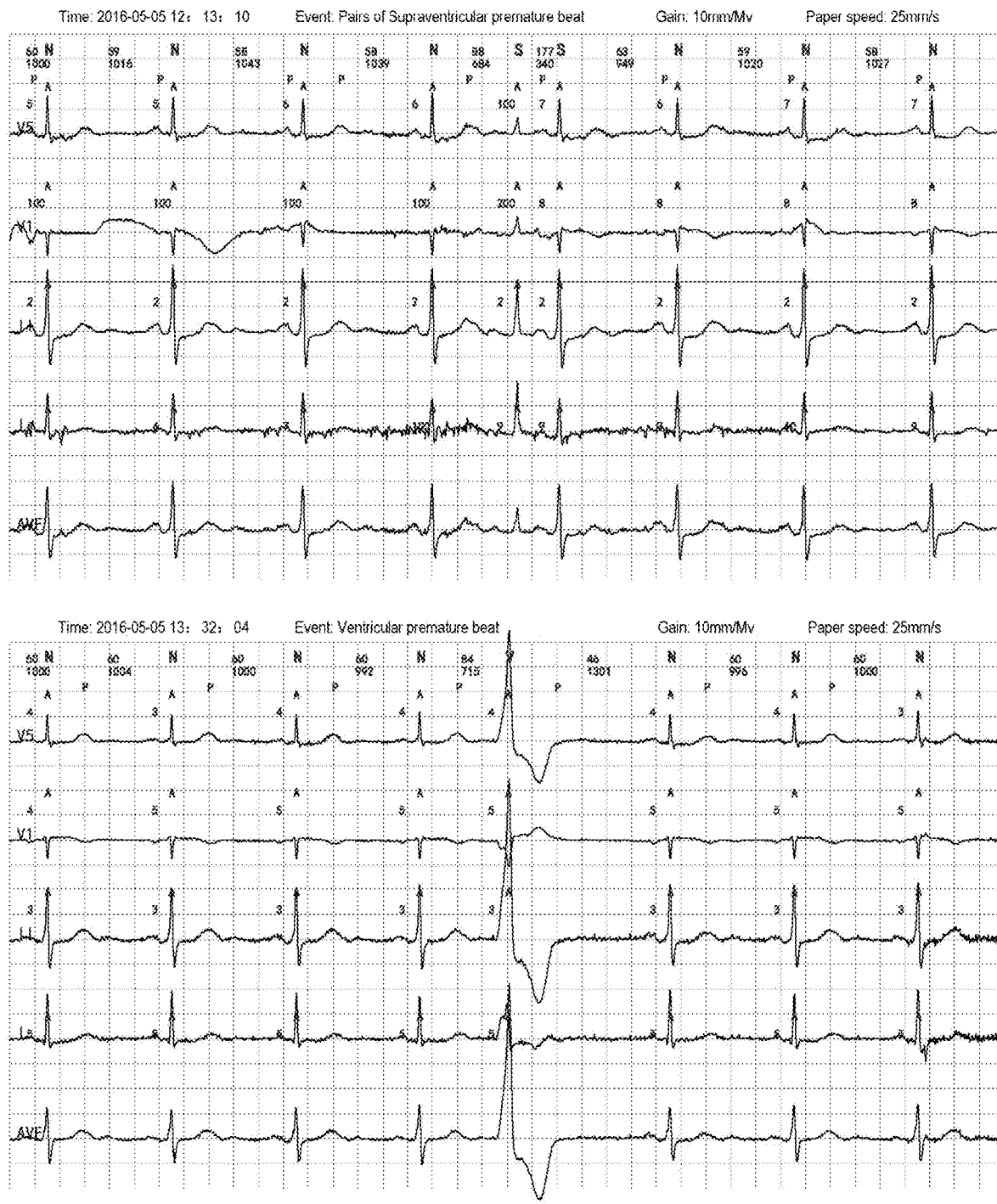
Figure 8E:
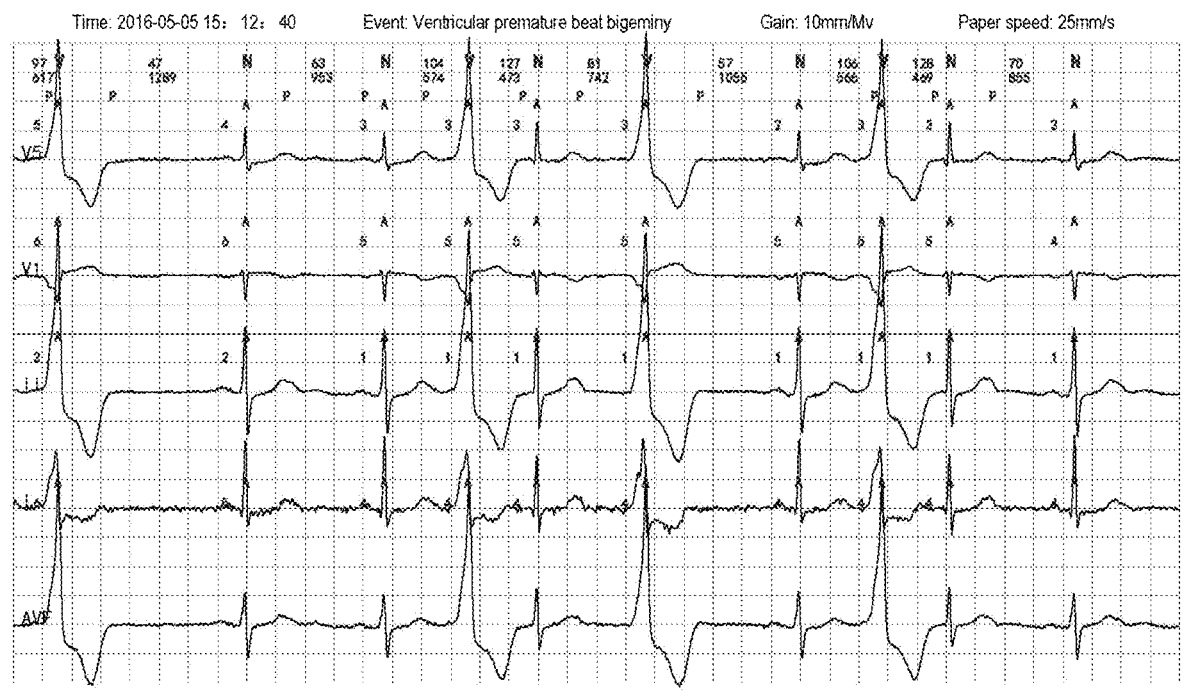
Figure 8E:
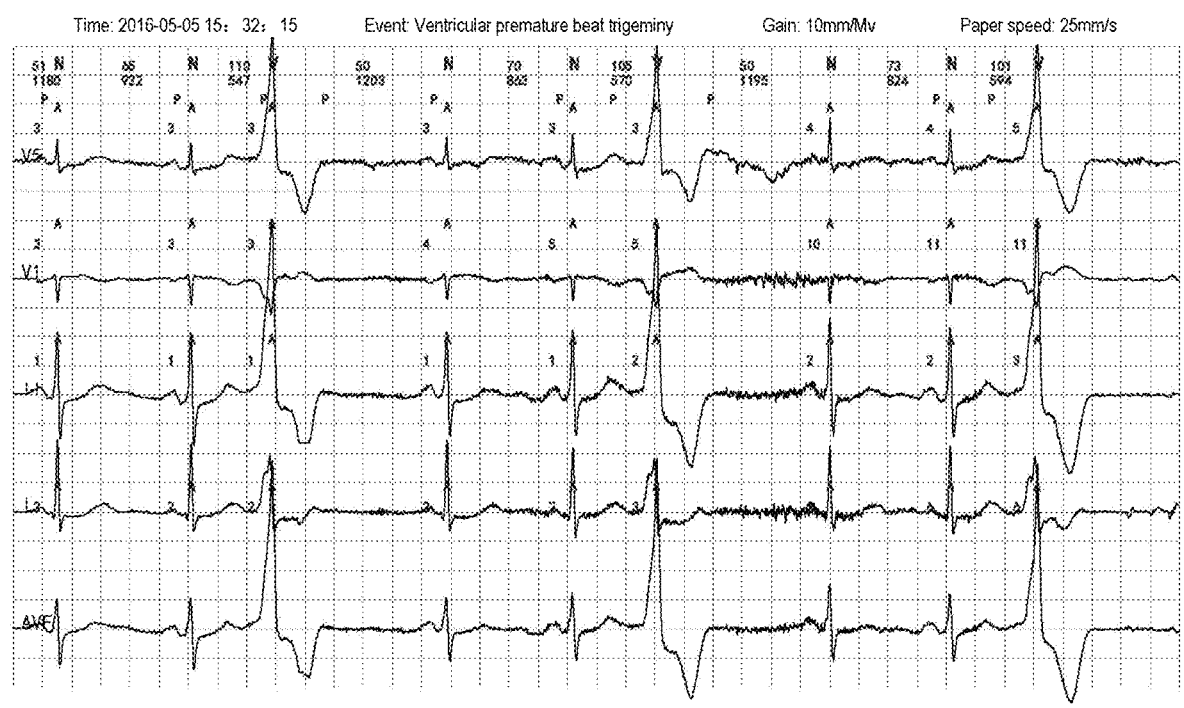
Figure 8F:
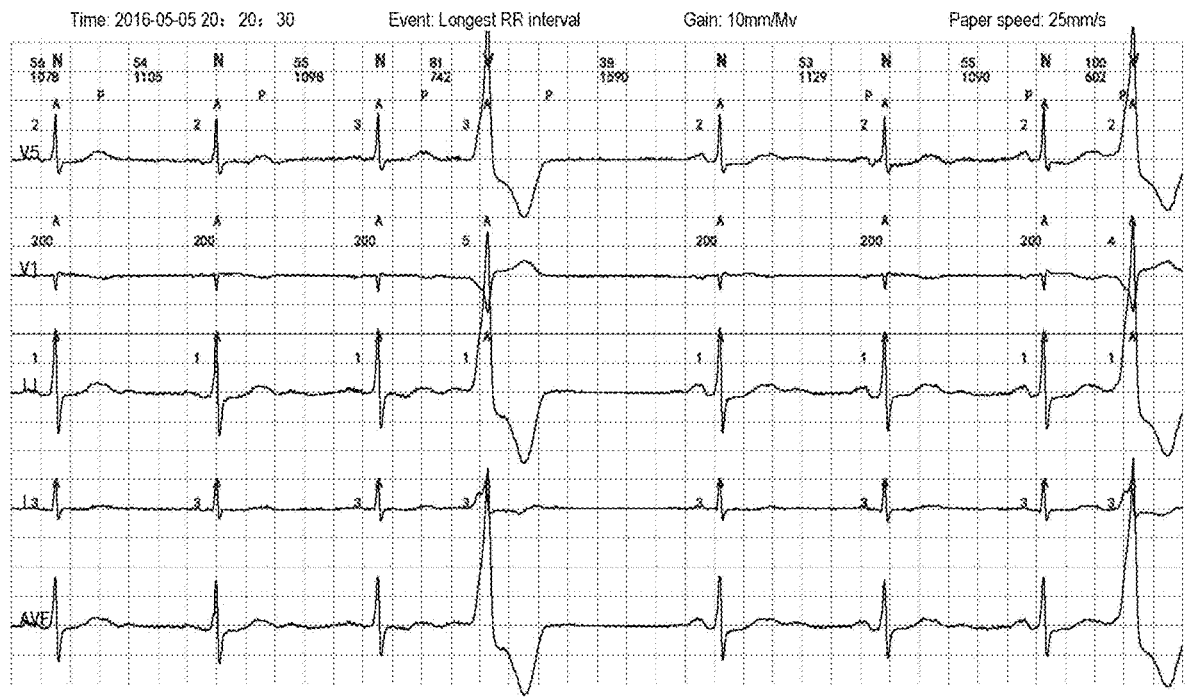

At the same time, the electrocardiogram workstation acquires the report output mode information and the output format information. The report output mode information refers to the format in which the report is output, and different report output modes may be provided according to different user authorities. For example, a user whose user category information is a patient, and only part of set data in the report data is output. The report output mode also includes how the output data is displayed. Different report output modes are shown in FIGS. 7a-7c and FIGS. 8a-8g, respectively, wherein FIGS. 7a-7c show a report output mode of resting electrocardiogram monitoring data, and FIGS. 8a-8g show a report output mode of ambulatory electrocardiogram monitoring data. The user may input or select corresponding report output mode information according to requirements, so that the electrocardiogram workstation outputs the report data in a corresponding output mode.

The output format information of the report may be an output format selected according to different purposes, which is used to convert the report data into a required data format and then output. Specific formats may include: Extensible Markup Language (XML), Standard Communication Protocol (SCP) for record and transmission of the electrocardiogram data, Portable Document Format (PDF), Joint Photographic Experts Group (JPEG), Digital Medical Imaging and Communication (DICOM) 3.0, electrocardiogram data annotation format (HI7) developed by HL7 and the like.

Default report output mode information and output format information are preset in the electrocardiogram workstation. When the user does not specify, the electrocardiogram workstation may convert the report data into the report output data according to the default format for output.

The output of the report output data includes the output on the human-computer interaction interface of the electrocardiogram workstation, print and output of a printer integrated or connected in the electrocardiogram workstation, etc.

Step 160: report conclusion modification data and/or report table item modification data input by the user are received; and the report conclusion data is updated according to the report conclusion modification data and the report table item data is updated according to the report table item modification data.

When the user has the authority to modify the report data, the report data may also be modified through the electrocardiogram workstation. The modification includes the modification of the report conclusion and the modification of the test data. In practical applications, this function is mainly open to doctors.

After obtaining the selected report data, if the electrocardiogram workstation receives the report conclusion modification data and/or the report table item modification data, the report data is first obtained and displayed through the human-computer interaction interface. At this time, the report data is in a readable and writable format.

After the user determines the content that needs to be modified according to the report data, the deletion on part of data in the original report data from the user is received through the human-computer interaction interface, and data newly input by the user is recorded, which may include the report conclusion data and the report table item data. After receiving the input data update instruction, the original report data is updated according to the data input by the user. Preferably, a record is generated in the report data, recording the time when the corresponding data is updated and the user ID for this operation.

Figure 6:
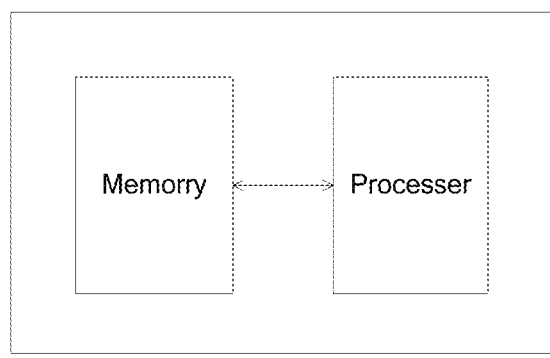
FIG. 6 is a schematic structure diagram illustrating an electrocardiogram workstation according to an embodiment of the present disclosure.

FIG. 6 is a schematic structure diagram illustrating an electrocardiogram workstation according to an embodiment of the present disclosure. The electrocardiogram workstation includes a processor and a memory. The memory may be connected to the processor via a bus. The memory may be a non-volatile memory, such as a hard disk drive and a flash memory, in which software programs and device drivers are stored. The software programs may perform various functions of the above method provided by the embodiment of the present disclosure. The device drivers may be a network and interface drivers. The processor is used for executing the software programs, and when the software programs are executed, the method provided by the embodiments of the present disclosure may be realized.

It should be noted that an embodiment of the present disclosure also provides a computer readable storage medium. The computer readable storage medium stores computer programs, and when the computer programs are executed by the processor, the method provided by the embodiments of the present disclosure may be realized.

An embodiment of the present disclosure further provides a computer program product including instructions. When the computer program product runs on a computer, the processor performs the above method.

In the artificial intelligence self-learning-based electrocardiogram information processing method and apparatus according to the embodiments of the present disclosure, through data preprocessing, heart beat feature detection, interference signal detection, signal quality evaluation and lead combination, heart beat classification, secondary classification of heart beat verification, classification of electrocardiogram events, and analysis and calculation of electrocardiogram parameters, the report data is finally automatically output. The method is a complete and fast process automatic analysis method. The automatic analysis method of the present disclosure may also record modification information of automatic analysis results and collect modified data to feed back to the deep learning model for continuous training, thus continuously improving and enhancing the accuracy rate of the automatic analysis method.

Those skilled in the art should further realize that the units and algorithm steps of the examples described in the embodiments disclosed herein may be implemented in electronic hardware, computer software, or a combination of the two. In order to clearly illustrate the interchangeability of hardware and software, the composition and steps of each example have been generally described according to functions in the above description. Whether these functions are implemented in hardware or software depends on the specific application and design constraints of the technical solutions. Those skilled in the art may use different methods to implement the described functions for each specific application, but such implementation should not be considered to be beyond the scope of the present disclosure.

The steps of methods or algorithm described in the embodiments disclosed herein may be implemented in hardware, a software module executed by a processor, or a combination of the two. The software module may be placed in random access memory (RAM), memory, read only memory (ROM), electrically programmable ROM, electrically erasable programmable ROM, registers, hard disks, removable disks, CD-ROM, or any other form of storage medium known in the technical field.

The specific embodiments described above have further explained the purpose, technical solution and beneficial effects of the present disclosure in detail. It should be understood that the above is only specific embodiments of the present disclosure and is not used to limit the scope of protection of the present disclosure. Any modification, equivalent substitution, improvement, etc., made within the spirit and principles of the present disclosure should be included in the scope of protection of the present disclosure.

What is claimed is:

1. An electrocardiogram information processing method, comprising:
   receiving, by an electrocardiogram workstation, electrocardiogram data output by an electrocardiogram monitoring device, wherein the electrocardiogram data comprises an identification ID of a tested object and detection time information and wherein the electrocardiogram data is single-lead or multi-lead time sequence data;
   performing electrocardiogram data analysis on the electrocardiogram data, and generating report data and storing the report data, wherein the performing electrocardiogram data analysis on the electrocardiogram data, and generating report data includes:
   converting a data format of the electrocardiogram data into a preset standard data format by resampling, and performing a first filtering processing on converted electrocardiogram data in the preset standard data format;
   performing heart beat detection processing on electrocardiogram data processed by the first filtering processing to identify multiple pieces of heart beat data comprised in the electrocardiogram data, each of which corresponds to a heart beat cycle, comprising amplitude data and starting-ending time data of corresponding P wave, QRS complex and T wave;
   performing interference identification on the heart beat data according to a trained Two-class interference identification model to determine whether there is interference in the heart beat data with a probability value for judging the interference;
   according to lead parameters of the heart beat data and the heart beat data, combining and generating heart beat time sequence data based on results of the interference identification and time rules; and generating heart beat analysis data according to the heart beat time sequence data;
   analyzing and evaluating a signal quality of the heart beat analysis data, and obtaining a signal quality evaluation index of the heart beat analysis data;
   performing feature extraction and analysis of an amplitude and time characterization data on the heart beat analysis data according to a trained heart beat classification model, to obtain primary classification information of the heart beat analysis data;
   inputting the heart beat analysis data of particular heart beats in results of the primary classification information into a trained ST segment and T wave change model for identification, and determining ST segment and T wave evaluation information;
   performing P wave and T wave feature detection on the heart beat analysis data according to the heart beat time sequence data to determine detailed feature information of the P wave and the T wave in each heart beat;
   performing secondary classification processing on the heart beat analysis data according to electrocardiogram basic rule reference data, the detailed feature information of the P wave and the T wave and the ST segment and T wave evaluation information under the primary classification information to obtain heart beat classification information; and
   generating electrocardiogram event data from the heart beat analysis data according to the heart beat classification information and the electrocardiogram basic rule reference data; screening the electrocardiogram event data according to the signal quality evaluation index to obtain the report conclusion data and the report table item data; and generating the report graphic data according to typical data segments in each kind of the electrocardiogram event data,
   wherein the report data comprises: report conclusion data, report table item data and/or report graphic data corresponding to the identification of the tested object;
   receiving a report data query instruction input by a user, querying corresponding report data according to the identification of the user, and generating report data query result list data to display and output; wherein the report data query result list data comprises at least the identification of the tested object and the detection time information of one or more pieces of the report data obtained by the querying;
   receiving a selection instruction input by the user, and acquiring selected report data according to the selection instruction; and
   receiving a report output instruction input by the user, determining output mode information and output format information according to the report output instruction, selectively outputting part or all of data in the report conclusion data, the report table item data and/or the report graphic data according to the output mode information, and performing data format conversion on the part or all of the data according to the output format information to generate report output data.

2. The method according to claim 1, wherein after the receiving a selection instruction input by the user, and acquiring selected report data according to the selection instruction, the method further comprises:
   receiving report conclusion modification data and/or report table item modification data input by the user; and
   updating the report conclusion data according to the report conclusion modification data, and updating the report table item data according to the report table item modification data.

3. The method according to claim 1, wherein the performing heart beat detection processing on electrocardiogram data processed by the first filtering processing further comprises:
   determining an RR interval according to the QRS complex and calculating an estimation value of noise in the RR interval; and
   determining a detection confidence level of each QRS complex according to the estimation value of the noise and a maximum amplitude in each QRS complex.

4. The method according to claim 1, wherein the performing interference identification on the heart beat data according to a trained Two-class interference identification model comprises:
performing cutting and sampling on the heart beat data with a first data amount, and inputting data obtained by the cutting and sampling into the Two-class interference identification model to identify interference;
identifying a data segment with a heart beat interval greater than or equal to a preset interval determination threshold in the heart beat data;
performing a judgment of signal abnormality on the data segment with the heart beat interval greater than or equal to the preset interval determination threshold to determine whether the data segment is an abnormal signal;
if the data segment is not an abnormal signal, according to a set time value, determining a starting data point and an ending data point of sliding sampling in the data segment with a preset time width, and performing the sliding sampling on the data segment from the starting data point until the ending data point to obtain multiple sample data segments; and
performing the interference identification on each of the multiple sample data segments.

5. The method according to claim 1, wherein the inputting the heart beat analysis data of particular heart beats in results of the primary classification information into a trained ST segment and T wave change model for identification, and determining ST segment and T wave evaluation information, comprises:
inputting data of the particular heart beats in the primary classification into the trained ST segment and T wave change model according to leads in turn, performing the feature extraction and analysis of the amplitude and time characterization data on the data of the particular heart beats of each lead to obtain ST segment and T wave change information of each lead, and determining the ST segment and T wave evaluation information, which is lead position information that indicates the ST segment and T wave corresponding to heart beat segment data occurs change.

6. The method according to claim 1, wherein the generating the report graphic data according to typical data segments in each kind of the electrocardiogram event data comprises:
performing evaluation on data segments in each kind of electrocardiogram event according to the signal quality evaluation index, and selecting the data segments with the highest signal quality evaluation index as the typical data segments in the electrocardiogram event.

7. An electrocardiogram workstation, comprising a memory and a processor, wherein the memory is used for storing programs including instructions, and the processor is used for executing the programs, wherein the instructions cause the electrocardiogram workstation to perform steps comprising:
receive electrocardiogram data output by an electrocardiogram monitoring device, wherein the electrocardiogram data comprises an identification ID of a tested object and detection time information and wherein the electrocardiogram data is single-lead or multi-lead time sequence data;
perform electrocardiogram data analysis on the electrocardiogram data, and generating report data and storing the report data including:
convert a data format of the electrocardiogram data into a preset standard data format by resampling, and performing a first filtering processing on converted electrocardiogram data in the preset standard data format;
perform heart beat detection processing on electrocardiogram data processed by the first filtering processing to identify multiple pieces of heart beat data comprised in the electrocardiogram data, each of which corresponds to a heart beat cycle, comprising amplitude data and starting-ending time data of corresponding P wave, QRS complex and T wave;
perform interference identification on the heart beat data according to a trained Two-class interference identification model to determine whether there is interference in the heart beat data with a probability value for judging the interference;
according to lead parameters of the heart beat data and the heart beat data, combine and generate heart beat time sequence data based on results of the interference identification and time rules; and generate heart beat analysis data according to the heart beat time sequence data;
analyze and evaluate a signal quality of the heart beat analysis data, and obtain a signal quality evaluation index of the heart beat analysis data;
perform feature extraction and analysis of an amplitude and time characterization data on the heart beat analysis data according to a trained heart beat classification model, to obtain primary classification information of the heart beat analysis data;
input the heart beat analysis data of particular heart beats in results of the primary classification information into a trained ST segment and T wave change model for identification, and determining ST segment and T wave evaluation information;
perform P wave and T wave feature detection on the heart beat analysis data according to the heart beat time sequence data to determine detailed feature information of the P wave and the T wave in each heart beat;
perform secondary classification processing on the heart beat analysis data according to electrocardiogram basic rule reference data, the detailed feature information of the P wave and the T wave and the ST segment and T wave evaluation information under the primary classification information to obtain heart beat classification information;
generate electrocardiogram event data from the heart beat analysis data according to the heart beat classification information and the electrocardiogram basic rule reference data; and
screen the electrocardiogram event data according to the signal quality evaluation index to obtain the report conclusion data and the report table item data; and generating the report graphic data according to typical data segments in each kind of the electrocardiogram event data,
wherein the report data comprises: report conclusion data, report table item data and/or report graphic data corresponding to the identification of the tested object;
receive a report data query instruction input by a user, query corresponding report data according to the identification of the user, and generate report data query result list data to display and output; wherein the report data query result list data comprises at least the identification of the tested object and the detection time information of one or more pieces of the report data obtained by the querying;

receive a selection instruction input by the user, and acquiring selected report data according to the selection instruction; and receive a report output instruction input by the user, determine output mode information and output format information according to the report output instruction, selectively output part or all of data in the report conclusion data, the report table item data and/or the report graphic data according to the output mode information, and performing data format conversion on the part or all of the data according to the output format information to generate report output data.

8. A computer program product comprising instructions, wherein when the computer program product runs on a computer, the instructions cause the computer to perform steps comprising:

receive electrocardiogram data output by an electrocardiogram monitoring device, wherein the electrocardiogram data comprises an identification ID of a tested object and detection time information and wherein the electrocardiogram data is single-lead or multi-lead time sequence data;

perform electrocardiogram data analysis on the electrocardiogram data, and generating report data and storing the report data including:

convert a data format of the electrocardiogram data into a preset standard data format by resampling, and performing a first filtering processing on converted electrocardiogram data in the preset standard data format;

perform heart beat detection processing on electrocardiogram data processed by the first filtering processing to identify multiple pieces of heart beat data comprised in the electrocardiogram data, each of which corresponds to a heart beat cycle, comprising amplitude data and starting-ending time data of corresponding P wave, QRS complex and T wave;

perform interference identification on the heart beat data according to a trained Two-class interference identification model to determine whether there is interference in the heart beat data with a probability value for judging the interference;

according to lead parameters of the heart beat data and the heart beat data, combine and generate heart beat time sequence data based on results of the interference identification and time rules; and generate heart beat analysis data according to the heart beat time sequence data;

analyze and evaluate a signal quality of the heart beat analysis data, and obtain a signal quality evaluation index of the heart beat analysis data;

perform feature extraction and analysis of an amplitude and time characterization data on the heart beat analysis data according to a trained heart beat classification model, to obtain primary classification information of the heart beat analysis data;

input the heart beat analysis data of particular heart beats in results of the primary classification information into a trained ST segment and T wave change model for identification, and determining ST segment and T wave evaluation information;

perform P wave and T wave feature detection on the heart beat analysis data according to the heart beat time sequence data to determine detailed feature information of the P wave and the T wave in each heart beat;

perform secondary classification processing on the heart beat analysis data according to electrocardiogram basic rule reference data, the detailed feature information of the P wave and the T wave and the ST segment and T wave evaluation information under the primary classification information to obtain heart beat classification information;

generate electrocardiogram event data from the heart beat analysis data according to the heart beat classification information and the electrocardiogram basic rule reference data; and screen the electrocardiogram event data according to the signal quality evaluation index to obtain the report conclusion data and the report table item data; and generating the report graphic data according to typical data segments in each kind of the electrocardiogram event data, wherein the report data comprises: report conclusion data, report table item data and/or report graphic data corresponding to the identification of the tested object;

receive a report data query instruction input by a user, query corresponding report data according to the identification of the user, and generate report data query result list data to display and output; wherein the report data query result list data comprises at least the identification of the tested object and the detection time information of one or more pieces of the report data obtained by the querying;

receive a selection instruction input by the user, and acquiring selected report data according to the selection instruction; and receive a report output instruction input by the user, determine output mode information and output format information according to the report output instruction, selectively output part or all of data in the report conclusion data, the report table item data and/or the report graphic data according to the output mode information, and performing data format conversion on the part or all of the data according to the output format information to generate report output data.

9. A computer readable storage medium, comprising instructions, wherein when the instructions run on a computer, the instructions cause the computer to perform steps comprising:

receive electrocardiogram data output by an electrocardiogram monitoring device, wherein the electrocardiogram data comprises an identification ID of a tested object and detection time information and wherein the electrocardiogram data is single-lead or multi-lead time sequence data;

perform electrocardiogram data analysis on the electrocardiogram data, and generating report data and storing the report data including:

convert a data format of the electrocardiogram data into a preset standard data format by resampling, and performing a first filtering processing on converted electrocardiogram data in the preset standard data format;

perform heart beat detection processing on electrocardiogram data processed by the first filtering processing to identify multiple pieces of heart beat data comprised in the electrocardiogram data, each of which corresponds to a heart beat cycle, comprising amplitude data and starting-ending time data of corresponding P wave, QRS complex and T wave;

perform interference identification on the heart beat data according to a trained Two-class interference identification model to determine whether there is interference in the heart beat data with a probability value for judging the interference;

according to lead parameters of the heart beat data and the heart beat data, combine and generate heart beat time sequence data based on results of the interference identification and time rules; and generate heart beat analysis data according to the heart beat time sequence data;

analyze and evaluate a signal quality of the heart beat analysis data, and obtain a signal quality evaluation index of the heart beat analysis data;

perform feature extraction and analysis of an amplitude and time characterization data on the heart beat analysis data according to a trained heart beat classification model, to obtain primary classification information of the heart beat analysis data;

input the heart beat analysis data of particular heart beats in results of the primary classification information into a trained ST segment and T wave change model for identification, and determining ST segment and T wave evaluation information;

perform P wave and T wave feature detection on the heart beat analysis data according to the heart beat time sequence data to determine detailed feature information of the P wave and the T wave in each heart beat;

perform secondary classification processing on the heart beat analysis data according to electrocardiogram basic rule reference data, the detailed feature information of the P wave and the T wave and the ST segment and T wave evaluation information under the primary classification information to obtain heart beat classification information;

generate electrocardiogram event data from the heart beat analysis data according to the heart beat classification information and the electrocardiogram basic rule reference data; and screen the electrocardiogram event data according to the signal quality evaluation index to obtain the report conclusion data and the report table item data; and generating the report graphic data according to typical data segments in each kind of the electrocardiogram event data, wherein the report data comprises: report conclusion data, report table item data and/or report graphic data corresponding to the identification of the tested object;

receive a report data query instruction input by a user, query corresponding report data according to the identification of the user, and generate report data query result list data to display and output; wherein the report data query result list data comprises at least the identification of the tested object and the detection time information of one or more pieces of the report data obtained by the querying;

receive a selection instruction input by the user, and acquiring selected report data according to the selection instruction; and receive a report output instruction input by the user, determine output mode information and output format information according to the report output instruction, selectively output part or all of data in the report conclusion data, the report table item data and/or the report graphic data according to the output mode information, and performing data format conversion on the part or all of the data according to the output format information to generate report output data.

\* \* \* \* \*